(12) United States Patent
Li et al.

(10) Patent No.: US 12,109,438 B2
(45) Date of Patent: Oct. 8, 2024

(54) POSITIONING METHOD REALIZED BY COMPUTER, AND RADIOTHERAPY SYSTEM

(71) Applicant: OUR UNITED CORPORATION, Xi'an (CN)

(72) Inventors: Jinsheng Li, Shenzhen (CN); Kaiqiang Fu, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 561 days.

(21) Appl. No.: 17/359,398

(22) Filed: Jun. 25, 2021

(65) Prior Publication Data
US 2021/0316156 A1    Oct. 14, 2021

Related U.S. Application Data

(63) Continuation-in-part of application No. PCT/CN2018/124001, filed on Dec. 26, 2018, and a
(Continued)

(51) Int. Cl.
*A61N 5/10* (2006.01)

(52) U.S. Cl.
CPC ........... *A61N 5/107* (2013.01); *A61N 5/1049* (2013.01); *A61N 5/1082* (2013.01)

(58) Field of Classification Search
CPC ..... A61N 5/1049; A61N 5/107; A61N 5/1082
See application file for complete search history.

(56) References Cited

U.S. PATENT DOCUMENTS 8,172,770 B2    5/2012  Mark
2005/0218341 A1*  10/2005  Saracen ............... A61N 5/1049
                                                          250/491.1
(Continued)

FOREIGN PATENT DOCUMENTS

CN    1070328 A    3/1993
CN    101843500 A  9/2010
(Continued)

OTHER PUBLICATIONS

China National Intellectual Property Administration, First office action of Chinese application No. 201880014415.0 issued on Aug. 25, 2021, which is a foreign counterpart application of this US application.
(Continued)

*Primary Examiner* — Blake C Riddick
(74) *Attorney, Agent, or Firm* — Knobbe, Martens, Olson & Bear, LLP

(57) ABSTRACT

A positioning method realized by a computer including acquiring a gamma angle for treatment; acquiring first coordinates of a treatment couch, the first coordinates being coordinates of the treatment couch when a preset shooting point coincides with an imaging point of an image guidance system (IGS); determining a first relative position between a target point of an affected part and the imaging point according to the gamma angle for treatment; acquiring a second relative position between the imaging point and an equipment isocenter; calculating second coordinates of the treatment couch at the gamma angle for treatment when the target point coincides with the equipment isocenter according to the first coordinates, the first relative position and the second relative position; and adjusting a position of the treatment couch according to the second coordinates.

13 Claims, 15 Drawing Sheets

Related U.S. Application Data continuation-in-part of application No. PCT/CN2018/123964, filed on Dec. 26, 2018.

(56) References Cited

U.S. PATENT DOCUMENTS

| | | | |
|---|---|---|---|
| 2007/0025524 A1* | 2/2007 | Yue | A61N 5/1049 378/205 |
| 2007/0041497 A1* | 2/2007 | Schnarr | A61N 5/103 378/65 |
| 2007/0123815 A1 | 5/2007 | Mark | |
| 2007/0127622 A1* | 6/2007 | Main | A61N 5/1049 378/64 |
| 2007/0195930 A1* | 8/2007 | Kapatoes | A61N 5/103 378/65 |
| 2008/0159478 A1* | 7/2008 | Keall | A61N 5/1042 378/65 |
| 2010/0054413 A1* | 3/2010 | Sobering | G16H 20/40 378/65 |
| 2010/0237257 A1* | 9/2010 | Saracen | A61B 6/0487 250/491.1 |
| 2011/0160589 A1* | 6/2011 | Fu | A61B 8/08 600/443 |
| 2011/0211665 A1* | 9/2011 | Maurer, Jr. | A61N 5/1039 378/19 |
| 2011/0313228 A1* | 12/2011 | Handa | G21K 5/10 600/1 |
| 2012/0008734 A1* | 1/2012 | Thomson | A61N 5/1049 378/22 |
| 2012/0069968 A1* | 3/2012 | Core | A61N 5/1049 378/206 |
| 2012/0071758 A1* | 3/2012 | Lachaine | A61B 8/085 600/443 |
| 2012/0106704 A1* | 5/2012 | Maurer, Jr. | G16H 20/30 378/65 |
| 2012/0109608 A1* | 5/2012 | Core | A61N 5/1067 703/6 |
| 2012/0312961 A1* | 12/2012 | Raleigh | A61B 6/542 250/206 |
| 2012/0316379 A1* | 12/2012 | Raleigh | A61N 5/1049 600/1 |
| 2012/0316423 A1* | 12/2012 | Raleigh | A61B 5/0077 600/407 |
| 2012/0316425 A1* | 12/2012 | Raleigh | A61N 5/1049 600/407 |
| 2013/0006036 A1* | 1/2013 | Raleigh | A61N 5/1077 382/128 |
| 2013/0006093 A1* | 1/2013 | Raleigh | A61B 6/584 600/407 |
| 2013/0235969 A1* | 9/2013 | Winter | A61N 5/1079 378/4 |
| 2013/0256551 A1* | 10/2013 | Yao | A61N 5/1082 250/393 |
| 2013/0267830 A1* | 10/2013 | Ojha | A61B 5/0035 600/1 |
| 2013/0317343 A1* | 11/2013 | Klimenko | A61B 5/0046 600/3 |
| 2014/0016759 A1* | 1/2014 | Ngar | G05B 19/4015 378/207 |
| 2014/0046212 A1 | 2/2014 | Deutschmann | |
| 2014/0235921 A1* | 8/2014 | Wendler | A61N 5/107 600/1 |
| 2015/0314137 A1* | 11/2015 | Maurer | A61N 5/1045 600/458 |
| 2016/0073980 A1 | 3/2016 | Yan et al. | |
| 2016/0114192 A1* | 4/2016 | Lachaine | A61B 6/032 600/1 |
| 2016/0199666 A1 | 7/2016 | Maurer et al. | |
| 2017/0128750 A1* | 5/2017 | Filiberti | A61N 5/1065 |
| 2017/0221206 A1* | 8/2017 | Han | G06T 7/11 |
| 2018/0056091 A1* | 3/2018 | Jordan | A61N 5/107 |
| 2018/0193668 A1* | 7/2018 | Jordan | A61N 5/1069 |
| 2018/0236267 A1* | 8/2018 | Kuang | A61B 6/5235 |
| 2018/0289982 A1* | 10/2018 | Sayeh | G16H 20/40 |
| 2018/0339173 A1* | 11/2018 | Kilby | A61N 5/1043 |
| 2018/0361172 A1* | 12/2018 | Zhang | A61N 5/1082 |
| 2019/0091487 A1* | 3/2019 | Pal | A61N 5/1069 |
| 2019/0117998 A1* | 4/2019 | Han | G06T 7/246 |
| 2019/0175122 A1* | 6/2019 | Stahl | A61B 6/5276 |
| 2019/0239844 A1* | 8/2019 | Bose | A61B 6/0492 |
| 2019/0282831 A1* | 9/2019 | Jordan | A61N 5/1039 |
| 2019/0381338 A1* | 12/2019 | Voronenko | A61N 5/1039 |
| 2020/0030633 A1* | 1/2020 | Van Heteren | A61N 5/1067 |
| 2020/0129785 A1* | 4/2020 | Li | A61N 5/1075 |
| 2020/0346036 A1* | 11/2020 | Li | A61N 5/1039 |
| 2020/0368555 A1* | 11/2020 | Gou | A61N 5/1069 |
| 2021/0339050 A1* | 11/2021 | Kaiser | A61N 5/107 |
| 2021/0346720 A1* | 11/2021 | Zhao | A61B 5/704 |

FOREIGN PATENT DOCUMENTS

| | | |
|---|---|---|
| CN | 202489969 U | 10/2012 |
| CN | 104587609 A | 5/2015 |
| CN | 105476634 A | 4/2016 |
| CN | 106408509 A | 2/2017 |
| CN | 108273199 A | 7/2018 |
| CN | 108635681 A | 10/2018 |
| CN | 108969906 A | 12/2018 |
| CN | 109068993 A | 12/2018 |
| JP | 2017035348 A | 2/2017 |

OTHER PUBLICATIONS

China National Intellectual Property Administration, Notification to grant patent right for invention application No. 201880014414.6 issued on Oct. 10, 2021, which is a foreign counterpart application of this US application.

International search report of PCT application No. PCT/CN2018/123964 issued on Sep. 18, 2019.

International search report of PCT application No. PCT/CN2018/124001 issued on Jul. 29, 2019.

* cited by examiner

POSITIONING METHOD REALIZED BY COMPUTER, AND RADIOTHERAPY SYSTEM

CROSS-REFERENCE TO RELATED APPLICATION

This application is a continuation in part application of international application No. PCT/CN2018/123964 and international application No. PCT/CN2018/124001, both filed on Dec. 26, 2018, the disclosure of each of which is incorporated herein by reference in its entirety.

TECHNICAL FIELD

The present disclosure relates to the field of radiotherapy technologies and, particularly, relates to a positioning method realized by a computer, and a radiotherapy system.

BACKGROUND

An image guidance system (IGS) may be adopted to accurately position a patient under image guidance before radiotherapy. During the positioning, a position deviation may be determined by performing image registration on an image obtained by the IGS system and a corresponding digitally reconstructed radio graph (DRR) image reconstructed by a pre-obtained computerized tomography (CT) image according to the image information, so that the patient may be accurately positioned by adjusting the position of a treatment couch. During the radiotherapy, a relative positional relationship between an equipment isocenter (i.e., a beam focus of the ray source) and a target point may be determined according to a relative positional relationship between an imaging point and the equipment isocenter and a relative positional relationship between a preset shooting point and the target point in the CT reconstructed image. Then, the position of the treatment couch may be adjusted according to the relative positional relationship between the equipment isocenter and the target point to align the target point of the affected part with the equipment isocenter, thereby facilitating the radiotherapy.

SUMMARY

According to a first aspect, provided is a positioning method realized by a computer, including:
  acquiring a gamma angle for treatment;
  acquiring first coordinates of a treatment couch, the first coordinates being coordinates of the treatment couch when a preset shooting point coincides with an imaging point of an image guidance system IGS;
  determining a first relative position between a target point of an affected part and the imaging point according to the gamma angle for treatment;
  acquiring a second relative position between the imaging point and an equipment isocenter;
  calculating second coordinates of the treatment couch at the gamma angle for treatment when the target point coincides with the equipment isocenter, according to the first coordinates, the first relative position and the second relative position; and
  adjusting a position of the treatment couch according to the second coordinates.

According to a second aspect, provided is a positioning apparatus, including:
  a first acquisition module, configured to acquire a gamma angle for treatment;
  a second acquisition module, configured to acquire first coordinates of a treatment couch, the first coordinates being coordinates of the treatment couch when a preset shooting point coincides with an imaging point of an image guidance system IGS;
  a first determination module, configured to determine a first relative position between a target point of an affected part and the imaging point according to the gamma angle for treatment;
  a third acquisition module, configured to acquire a second relative position between the imaging point and an equipment isocenter;
  a calculation module, configured to calculate second coordinates of the treatment couch at the gamma angle for treatment when the target point coincides with the equipment isocenter, according to the first coordinates, the first relative position and the second relative position; and
  a first adjustment module, configured to adjust a position of the treatment couch according to the second coordinates.

According to a third aspect, provided is a positioning apparatus, including:
  a processor and a memory in which instructions are stored, wherein the instructions are loaded and executed by the processor to implement the positioning method according to the first aspect.

According to a fourth aspect, provided is a storage medium in which instructions are stored, wherein when the storage medium runs at a processing component, the processing component is actuated to execute the positioning method according to the first aspect.

According to a fifth aspect, provided is a radiotherapy system, including the positioning apparatus according to the second aspect.

It should be understood that the above general description and the following detailed description are merely examples and are explanatory, and thereby do not limit the present disclosure.

BRIEF DESCRIPTION OF DRAWINGS

To describe the technical solutions in the embodiments of the present disclosure more clearly, the following briefly introduces the accompanying drawings required for describing the embodiments. Apparently, the accompanying drawings in the following description show merely some embodiments of the present disclosure, and a person of ordinary skill in the art may still derive other drawings from these accompanying drawings without creative efforts.

Through the aforesaid drawings, certain embodiments of the present disclosure have been shown and will be described in more detail below. The drawings and written description are not intended to limit the scope of the concepts of the present disclosure in any way, but rather to illustrate the concepts of the present disclosure to a person of ordinary skill in the art by referring to specific embodiments.

DESCRIPTION OF EMBODIMENTS

In the related arts, for the sake of preventing the treatment beam from affecting sensitive tissues or organs (such as, eyes) outside the affected part during the radiotherapy, the patient's position is generally adjusted by adjusting a gamma angle of the radiotherapy system so that the treatment beam can avoid the sensitive parts. The gamma angle herein may refer to an angle between a vertical surface and a support surface of a gamma angle adjustment device at the bottom of the patient for supporting the patient.

However, the gamma angle is fixed at 90°, since the patient generally lies flat when taking the CT image. If the gamma angle is adjusted during the radiotherapy, the accuracy of the positioning performed by the IGS system according to the reconstructed image of the CT image will be greatly reduced, thereby seriously affecting the radiotherapy effect.

In order to make the objectives, technical solutions and advantages of the present disclosure clearer, the embodiments of the present disclosure will be described in detail below with reference to the accompanying drawings.

Figure 1:
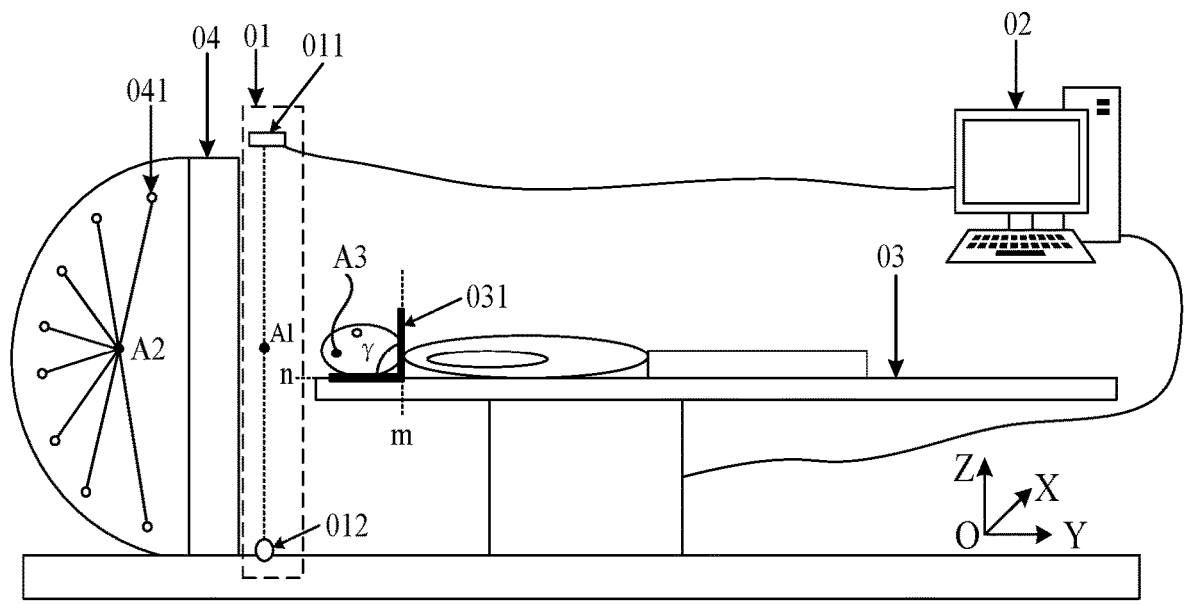
FIG. 1 is a schematically structural diagram of a radiotherapy system according to an embodiment 1 of the present disclosure.

FIG. 1 is a schematically structural diagram of a radiotherapy system according to an embodiment 1 of the present disclosure. As shown in FIG. 1, the radiotherapy system may include an image guidance system 01, a host computer 02, a treatment couch 03, and a treatment gantry 04. The host computer 02 may establish a communication connection with the image guidance system 01 and the treatment couch 03.

The host computer 02 may be a control equipment of a treatment control system, and the image guidance system 01 may be an IGS system. The IGS system 01 may include one or more groups of image collection components, and each group of the image collection components may include a detector 011 and a tube 012 that are disposed opposite to each other (FIG. 1 merely illustrates one group of the detector 011 and tube 012 that are disposed opposite to each other). The tube 012 may emit rays (for example, X-rays), and the detector 011 may be a flat panel detector and receive rays emitted by the tube 012. The IGS system 01 may generate an IGS image according to rays received by each detector 011. When the IGS system 01 includes one group of image collection components, the detector 011 and the tube 012 that are disposed opposite to each other may rotate to multiple positions and produce IGS images at the multiple positions. The embodiment 1 of the present disclosure is illustrated by taking an example where the IGS system 01 includes multiple groups of image collection components and may for example include two groups of image collection components. The rays emitted by the tube 012 in the multiple groups of image collection components of the IGS system 01 may intersect at a point, and the point is the imaging point A1 of the IGS system.

Figure 2:
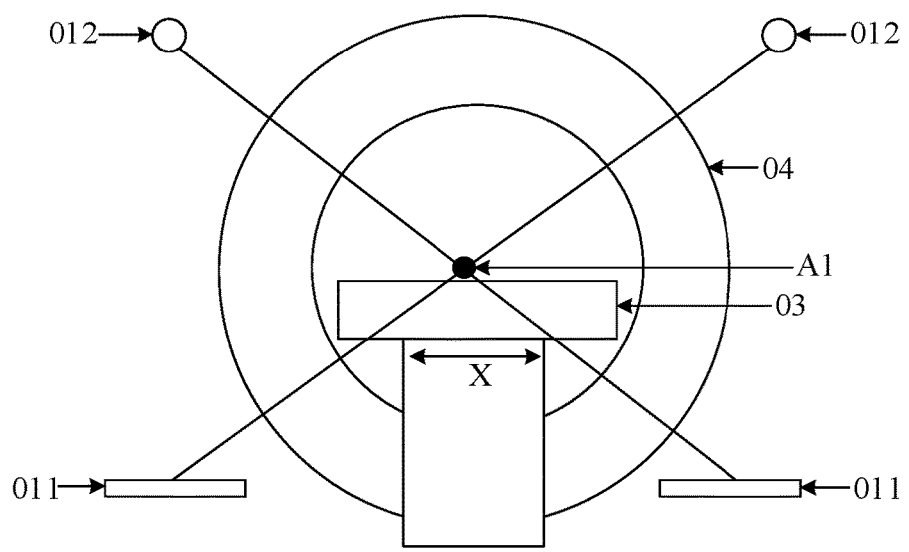
FIG. 2 is a front view of a radiotherapy system including two groups of image collection components according to the embodiment 1 of the present disclosure.

For example, FIG. 2 is a front view of a radiotherapy system including two groups of image collection components according to the embodiment 1 of the present disclosure. With reference to FIG. 2, each group of the image collection components includes a detector 011 and a tube 012 that are disposed opposite to each other. The rays emitted by the tubes 012 in the two groups of image collection components intersect at a point A1, and the point A1 is the imaging point.

Furthermore, with reference to FIG. 1, the treatment gantry 04 may be provided with multiple ray sources 041, and the multiple ray sources 041 may all be γ-ray sources (that is, the multiple ray sources 041 may all emit γ rays) or X-ray sources (that is, the multiple ray sources 041 may all emit X rays). The treatment beams emitted by the multiple ray sources 041 may intersect at a point, and the point is a beam focus (also may be referred to as the equipment isocenter) A2.

Before the radiotherapy, a patient is generally subjected to CT scanning to obtain a CT image of the affected part, and then a CT reconstructed image is acquired according to the CT image. Of course, the patient may also be subjected to MR (magnetic resonance) scanning before the radiotherapy to obtain MR images or the like of the patient. The embodiment 1 of the present disclosure takes CT as an example for illustration. A therapist may formulate a treatment plan for the affected part according to a size and a shape of the affected tumor, and surrounding tissues displayed in the CT reconstructed image, and input the treatment plan to the host computer 02. Then, the host computer 02 may drive the treatment couch 03 to move the affected part of the patient to an imaging area of the IGS system 01 to obtain images. Thereafter, the relative position between the preset shooting point in the CT reconstructed image (namely, a fixed point predetermined in the CT reconstructed image) and the imaging point A1 of the IGS system 01 may be determined by comparing the IGS image acquired by the IGS system 01 with the CT reconstructed image acquired in advance.

Furthermore, the host computer 02 may adjust the position of the treatment couch 03 to cause the preset shooting point to coincide with the imaging point A1 of the IGS system 01. During the radiotherapy, the host computer 02 may determine the positional relationship between the target point A3 and the equipment isocenter A2 according to the relative positional relationship between the equipment isocenter A2 and the imaging point A1 and the relative positional relationship between the preset shooting point in the CT reconstructed image and the target point A3. Then, the host computer 02 may adjust the position of the treatment couch 03 according to the positional relationship between the target point A3 and the equipment isocenter A2 to align the target point A3 with the equipment isocenter A2, thereby realizing positioning of the patient.

However, since the patient generally lies flat on the treatment couch 03 during the CT positioning scan, the treatment beam may pass through the patient's sensitive tissues or organs, such as eyes, so as to irradiate the target point A3. Thus, as shown in FIG. 1, the therapist may adjust the patient's posture with the gamma angle adjustment device 031 or the like to cause the treatment beam to avoid the sensitive tissues or organs. The gamma angle adjustment device 031 is able to rotate in a vertical plane, such as, in a YOZ plane shown in FIG. 1, around a fixed gamma angle rotation axis. An axis of the gamma angle rotation axis is parallel to the horizontal plane and perpendicular to the length direction of the treatment couch 03. The angle γ between a vertical plane m and a support surface n of a support part for supporting the patient in the gamma angle adjustment device 031 may be referred to as the gamma angle.

For example, the CT image is acquired by scanning the patient lying flat (that is, the gamma angle γ is 90°). In the actual treatment process, if the therapist selects a gamma angle of 70° and the IGS system 01 is used for positioning, it is required to adjust the patient's head to be at a gamma angle of 70° by adjusting the gamma angle adjustment device 031 and then collect the IGS image. Due to deflection of the patient's posture, the offset cannot be acquired by directly comparing the acquired CT reconstructed image with the acquired IGS image at this point, thereby failing to achieve accurate positioning and accurate treatment. Thus, when the gamma angle is adjusted during the radiotherapy, the positioning situation at the gamma angle is required to be taken into consideration, that is, it is required to consider coordinates of the treatment couch to be positioned at the gamma angle, so that the accuracy of the positioning at different gamma angles can be ensured and the accuracy of the treatment can be further ensured.

Embodiment 1

The embodiment 1 of the present disclosure provides a positioning method realized by a computer, which is capable of calculating coordinates of the treatment couch 03 at different gamma angles when the target point A3 coincides with the equipment isocenter A2. In this way, even after the gamma angle changes, the host computer 02 can also accurately adjust position of the treatment couch 03 according to the calculated coordinates of the treatment couch 03, which improves the accuracy of the alignment between the target point A3 and the equipment isocenter A2 and further improves the accuracy of the radiotherapy.

Figure 3:
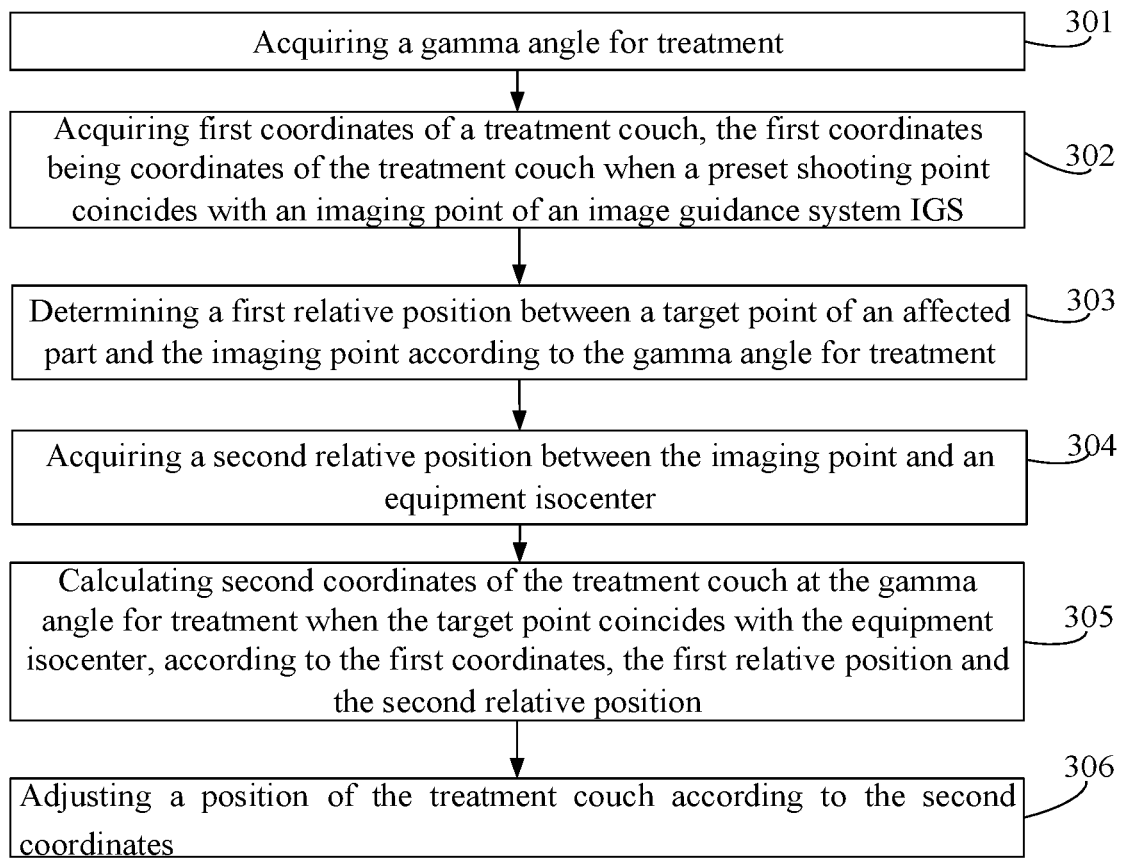
FIG. 3 is a flowchart of a positioning method according to the embodiment 1 of the present disclosure.

FIG. 3 is a flowchart of a positioning method realized by a computer according to the embodiment 1 of the present disclosure. The positioning method may be applied to the host computer 02 shown in FIG. 1. As shown in FIG. 3, the method may include following steps.

In step 301, a gamma angle for treatment is acquired.

In the embodiment 1 of the present disclosure, the gamma angle for treatment may be a current gamma angle for treatment.

For example, the therapist may fix the patient at a certain gamma angle through the gamma angle adjustment device 031 and input the current gamma angle to the host computer 02. That is, the host computer 02 may acquire the gamma angle γ for treatment input by the therapist. Alternatively, when the therapist fixes the patient at a certain gamma angle through the gamma angle adjustment device 031, the host computer 02 may detect the gamma angle γ for treatment automatically. Further alternatively, the host computer 02 may determine the gamma angle γ for treatment according to the treatment plan acquired in advance. The embodiment 1 of the present disclosure does not limit the manner in which the host computer 02 acquires the gamma angle for treatment.

In step 302, first coordinates of the treatment couch are acquired. The first coordinates are coordinates of the treatment couch when a preset shooting point coincides with an imaging point of the IGS.

For example, the host computer 02 may acquire the CT reconstructed image at the gamma angle for treatment. The CT reconstructed image may be an image which is reconstructed by the IGS system 01 according to an electronic image of the affected part acquired in advance, that is, an image of the patient before the treatment such as a CT image. The CT reconstructed image may include the preset shooting point. Then, when the host computer 02 drives the treatment couch 03 to send the affected part of the patient into the imaging area (i.e., the shooting area), the IGS system 01 may obtain the IGS image of the affected part of the patient and send the acquired IGS image to the host computer 02.

In order to determine whether the preset shooting point coincides with the imaging point A1, the host computer 02 may perform image registration on the acquired IGS image and the CT reconstructed image, and continuously adjust the position of the treatment couch 03 during the registration process, so as to finally enable the preset shooting point to coincide with the imaging point A1. When the preset shooting point coincides with the imaging point, the host computer 02 may acquire the first coordinates of the treatment couch 03 at this point.

In step 303, a first relative position between a target point of the affected part and the imaging point is determined according to the gamma angle for treatment.

In the embodiment 1 of the present disclosure, the host computer 02 may determine the position of the target point A3 according to the treatment plan.

For example, before the radiotherapy, the host computer 02 may acquire the CT reconstructed image at different gamma angles for treatment. According to the CT reconstructed image, the therapist may formulate a treatment plan for the patient, which includes positions of the target point A3 and the preset shooting point, and input the treatment plan to the host computer 02, so that the host computer 02 may acquire the position of the target point A3 from the treatment plan. Since the position of the imaging point A1 is fixed, the host computer 02 may directly obtain the position of the imaging point A1. In addition, since the target point A3 and the imaging point A1 are located in different coordinate systems, the host computer 02 may also convert the positions of the target point A3 and the imaging point A1 into a same coordinate system to calculate the first relative position between the target point A3 and the imaging point A1.

In step 304, a second relative position between the imaging point and the equipment isocenter is acquired.

The position of the equipment isocenter A2 is also fixed in the radiotherapy system. Thus, the host computer 02 may acquire the position of the equipment isocenter A2 directly. In addition, since the imaging point A1 and the equipment isocenter A2 are located in the same coordinate system, the host computer 02 may directly calculate a second relative position between the imaging point A1 and the equipment isocenter A2 according to the acquired positions of the imaging point A1 and the equipment isocenter A2.

In step 305, when the target point coincides with the equipment isocenter, second coordinates of the treatment couch at the gamma angle for treatment are calculated according to the first coordinates, the first relative position and the second relative position.

After acquiring the first coordinates, the first relative position and the second relative position, the host computer 02 may accurately calculate and obtain the second coordinates of the treatment couch at the gamma angle for treatment when the target point coincides with the equipment isocenter according to the first coordinates, the first relative position and the second relative position.

In step 306, the position of the treatment couch is adjusted according to the second coordinates.

Furthermore, the host computer 02 may accurately adjust the position of the treatment couch 03 according to the calculated second coordinates, which improves the accuracy of the alignment between the target point A3 and the equipment isocenter A2 at the gamma angle for treatment, thereby improving the accuracy of the radiotherapy.

In summary, the embodiment 1 of the present disclosure provides a positioning method realized by a computer. According to the method, when the target point coincides with the equipment isocenter, the second coordinates of the treatment couch at the gamma angle for treatment can be calculated according to the first coordinates of the treatment couch acquired when the preset shooting point coincides with the imaging point, the first relative position between the target point of the affected part and the imaging point, and the second relative position between the imaging point and the equipment isocenter. Then, the position of the treatment couch can be adjusted according to the second coordinates. Therefore, after adjusting the gamma angle during the radiotherapy, the second coordinates of the treatment couch at the adjusted gamma angle can be accurately calculated when the target point coincides with the equipment isocenter, which improves the accuracy of the alignment between the target point and the equipment isocenter at different gamma angles and improves the accuracy of the radiotherapy.

It should be noted that the embodiment 1 of the present disclosure is illustrated by taking an example where the host computer 02 has a communication connection with the IGS system 01 and the treatment couch 03 and the steps 301 to 306 are executed through the host computer 02. During the actual execution process, the treatment couch 03 and the IGS system 01 may be respectively provided with processors, and the treatment couch 03 and the IGS system 01 may execute the corresponding steps in the aforesaid embodiment 1 through their respective processors correspondingly, which is not limited in the embodiment 1 of the present disclosure. Only FIG. 3 and the aforesaid embodiment 1 are taken as examples for illustration herein.

Figure 4:
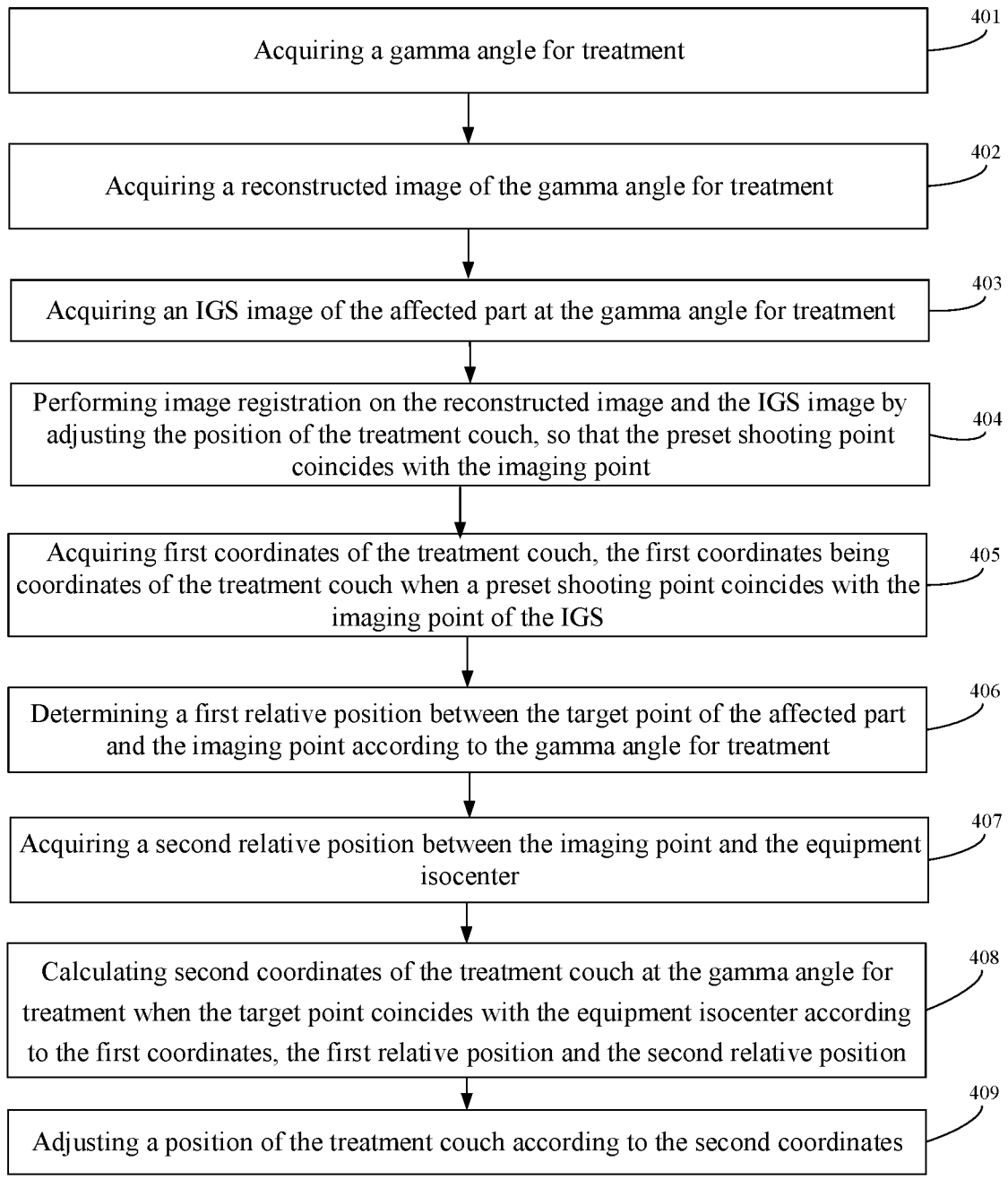
FIG. 4 is a flowchart of another positioning method according to the embodiment 1 of the present disclosure.

FIG. 4 is a flowchart of another positioning method realized by a computer according to the embodiment 1 of the present disclosure. The positioning method may be applied to the host computer 02 shown in FIG. 1. Alternatively, with reference to above description, the positioning method may also be applied to the IGS system 01 or the treatment couch 03 shown in FIG. 1, which is not limited in the embodiment 1 of the present disclosure. The following embodiment is illustrated by taking the positioning method applied to the host computer 02 as an example. As shown in FIG. 4, the method may include following steps.

In step 401, a gamma angle for treatment is acquired.

In the embodiment 1 of the present disclosure, the gamma angle for treatment may be a current gamma angle for treatment.

As an implementation, the therapist may fix the patient at a certain gamma angle through the gamma angle adjustment device 031 and input the current gamma angle γ to the host computer 02. That is, the host computer 02 may acquire the gamma angle γ for treatment input by the therapist. Such an acquiring method is relatively reliable.

As another implementation, when the therapist fixes the patient at a certain gamma angle γ through the gamma angle adjustment device 031, the host computer 02 may detect the gamma angle γ for treatment automatically. Such an acquiring method is relatively efficient.

As still another implementation, the host computer 02 may determine the gamma angle γ for treatment according to the treatment plan acquired in advance.

For example, assuming that the current gamma angle γ for treatment is 70°, the therapist may adjust the gamma angle γ to be 70° by adjusting the gamma angle adjustment device 031 shown in FIG. 1. After completing the fixing of the gamma angle adjustment device 031, the therapist may input the gamma angle γ for treatment to the host computer 02 as γ=70°, and then the gamma angle γ for treatment acquired by the host computer 02 is 70°.

In step 402, a reconstructed image of the gamma angle for treatment is acquired.

In the embodiment 1 of the present disclosure, the reconstructed image may be an image reconstructed from an electronic image (such as, a CT image) of the affected part acquired in advance. The reconstructed image may be an image reconstructed by the IGS system 01 according to the electronic image. Alternatively, the reconstructed image may be an image reconstructed by an electronic image generation device (for example, a CT device) according to the electronic image. Further alternatively, the reconstructed image may be a reconstructed image generated by other image processing systems according to the electronic image. The embodiment 1 of the present disclosure does not limit the device that generates the reconstructed image.

Figure 5:
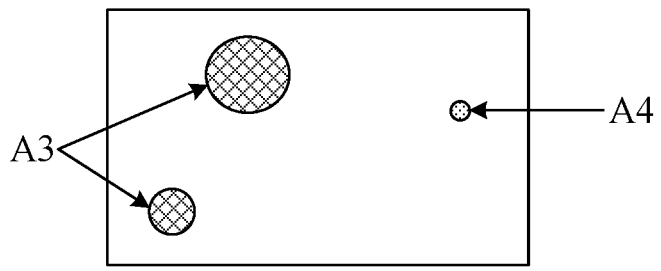
FIG. 5 is a schematic diagram of an acquired CT reconstructed image including a target point and a preset shooting point according to the embodiment 1 of the present disclosure.

For example, the reconstructed image may be a digitally reconstructed radiological image (DRR image), and the DRR image may be an image reconstructed by the IGS system 01 according to the CT image after acquiring the CT image of the affected part. Correspondingly, the reconstructed image may also be referred to as a CT-DRR film. With reference to FIG. 5, the CT-DRR film may include positions of the target point A3 and the preset shooting point A4. FIG. 5 shows the CT-DRR film including two target points A3.

For example, the electronic image acquired by the IGS system 01 may be a plurality of continuous tomographic images acquired by scanning the affected part with a CT device. That is, the electronic image may be a group of image sequences. Each tomographic image in the image sequence is perpendicular to the horizontal axis of the treatment couch 03, and an extension direction of the horizontal axis may be parallel to a movement direction (that is, a forward direction) of the treatment couch 03 while moving close to a treatment chamber. Since each tomographic image is a two dimensional image, the plurality of continuous tomographic images may be reconstructed as three dimensional (3D) volume data of the affected part through computer processing. For example, the layer thickness of the CT device may be no more than 2 mm when scanning the affected part, and there is no interlayer spacing.

During the process of image reconstruction, the IGS system 01 may determine the rotation axis firstly according to the preset shooting point A4 in the CT image. The rotation axis may be a designated coordinate axis of the coordinate system where the shooting point A4 is located, or a linear axis parallel to the designated coordinate axis. For example, the linear axis passing through the shooting point A4 and parallel to the designated coordinate axis (such as, the X axis) in the coordinate system where the shooting point A4 is located may be determined as the rotation axis. Furthermore, for each gamma angle, the IGS system 01 may rotate the CT image by a deflection angle by taking the rotation axis as the axis to reconstruct the reconstructed image of the gamma angle. The deflection angle is a deflection angle between the gamma angle and an initial gamma angle when the electronic image is collected. Specifically, the IGS system 01 may rotate the 3D volume data corresponding to the plurality of tomographic images by the deflection angle by taking the rotation axis as the axis, and project the rotated 3D volume data on a virtual imaging surface of the IGS system 01 according to installation parameters of the IGS system 01, thereby obtaining the reconstructed image of the gamma angle.

The shooting point A4 in the CT image is a preset point in the CT image, and the position of the shooting point A4 may be described by coordinates of the three coordinate axes in the 3D coordinate system where the shooting point A4 is located. The virtual imaging surface is an imaging surface of the IGS system 01 constructed virtually in the coordinate system where the shooting point A4 is located. The position of the virtual imaging surface in the 3D coordinate system where the shooting point A4 is located is the same as the position of the imaging surface of the detector of the IGS system 01 in the coordinate system (also referred to as an equipment coordinate system) where the treatment couch 03 is located.

For example, as described above, the IGS system 01 may include multiple groups of image collection components, and each group of image collection components may include a detector 011 and a tube 012 that are disposed opposite to each other. The installation parameters of each group of the image collection components may affect the virtual imaging surface when the IGS system 01 generates the reconstructed image. Thus, prior to projecting the rotated 3D volume data on the virtual imaging surface of the IGS system 01, the IGS system 01 may determine the position of the virtual imaging surface of the IGS system 01 in the coordinate system where the shooting point is located according to the installation parameters of the image collection components. The installation parameters may include: an angle between the rays of two groups of image collection components, a distance between the detector 011 and the tube 012 in each group of the image collection components, and a distance between an intersection of the rays and the detector 011, and the like. The rays of each group of the image collection components may be a connection line between the detector 011 and the tube 012 in the group of image collection components, and the imaging surface of the detector 011 is perpendicular to the rays emitted by the tube 012.

It should be noted that: when rotating the 3D volume data to reconstruct the reconstructed image of a certain gamma angle, the rotation direction of the 3D volume data may be determined according to the deflection direction of the gamma angle relative to the initial gamma angle when the CT image is acquired, so as to ensure that the rotation direction of the 3D volume data in the image coordinate system is consistent with the deflection direction of the gamma angle in the coordinate system where the treatment couch 03 is located, and the deflection angles are al so consistent.

Furthermore, the IGS system 01 may send the reconstructed CT-DRR films of the plurality of gamma angles to the host computer 02. After acquiring the gamma angle for treatment, the host computer 02 may take the reconstructed image of the gamma angle for treatment from the reconstructed image of at least one gamma angle.

For example, the host computer 02 may take the reconstructed image of the gamma angle γ for treatment from the plurality of reconstructed images received in advance after acquiring the current gamma angle for treatment. For example, the IGS system 01 may reconstruct the reconstructed images at angles of 60°, 70°, 80°, 90°, 100°, and 110° according to the CT image, and send all the reconstructed images corresponding to the plurality of gamma angles to the host computer 02. The host computer 02 may take the reconstructed image at the gamma angle of 70° directly if the current gamma angle γ for treatment as acquired is 70°.

In step 403, an IGS image of the affected part at the gamma angle for treatment is acquired.

The IGS image is an image generated by the image guidance system 01 (i.e., IGS system 01). The host computer 02 may adjust the position of the treatment couch 03 according to the fixed coordinate values set in advance, and send the affected part of the patient into the imaging area of the IGS system. Since the current patient has been fixed at the gamma angle for treatment, the IGS system 01 may acquire the IGS image of the affected part at the gamma angle γ for treatment directly through the multiple groups of image collection components, and send the acquired IGS image to the host computer 02.

For example, the host computer 02 may send imaging instructions to the IGS system 01, and the IGS system 01 may control the two tubes 012 shown in FIG. 2 to emit rays after receiving the imaging instructions. Correspondingly, the two detectors 011 shown in FIG. 2 may both receive the rays emitted by the tubes 012, and the IGS system 01 may generate the IGS image according to the rays received by each detector 011 and send the IGS image to the host computer 02.

In step 404, an image registration is performed on the reconstructed image and the IGS image by adjusting the position of the treatment couch, so that the preset shooting point coincides with the imaging point.

In the embodiment 1 of the present disclosure, in order to determine whether the preset shooting point A4 in the reconstructed image (i.e., CT-DRR film) coincides with the imaging point A1, the host computer 02 may perform an image registration on the CT-DRR film and the IGS image, and continuously adjust the position of the treatment couch 03 during the image registration process, so as to finally cause the preset shooting point A4 to coincide with the imaging point A1.

Generally, one image is designated as a reference image during the process of image registration, and another image is an image to be registered. The purpose of registration is to enable coordinates of all points on the image to be registered to be consistent with coordinates of the points on the reference image.

In step 405, first coordinates of the treatment couch are acquired. The first coordinates are coordinates of the treatment couch when the preset shooting point coincides with the imaging point of the IGS.

When the preset shooting point A4 coincides with the imaging point A1, the host computer 02 may acquire the first coordinates of the treatment couch 03 at this point. The first coordinates may include a first dimensional coordinate X1 extending in a width direction of the treatment couch 03, a second dimensional coordinate Y1 extending in a length direction of the treatment couch 03, and a third dimensional coordinate Z1 extending in a height direction of the treatment couch 03. That is, the first coordinates may be expressed as (X1, Y1, Z1).

In step 406, a first relative position between a target point of the affected part and the imaging point is determined according to the gamma angle for treatment.

In the embodiment 1 of the present disclosure, the host computer 02 may determine the position of the target point A3 of the affected part according to the treatment plan firstly.

For example, before the radiotherapy, the host computer 02 may acquire the CT-DRR films at different gamma angles for treatment. According to the CT-DRR films, the therapist may formulate a treatment plan for the patient, which includes the positional relationship between the target point A3 and the shooting point A4, and input the treatment plan to the host computer 02, so that the host computer 02 may acquire the position of the target point A3 from the treatment plan. For example, the host computer 02 may obtain the CT-DRR films at the gamma angles of 70°, 90° or 110° for treatment. Secondly, since the position of the imaging point A1 is fixed, the host computer 02 may directly obtain the position of the imaging point A1. Finally, since the target point A3 and the imaging point A2 are located in different coordinate systems, the host computer 02 may convert the position of the acquired target point A3 and the position of the imaging point A1 into a same coordinate system to calculate the first relative position between the target point A3 and the imaging point A1.

Figure 6:
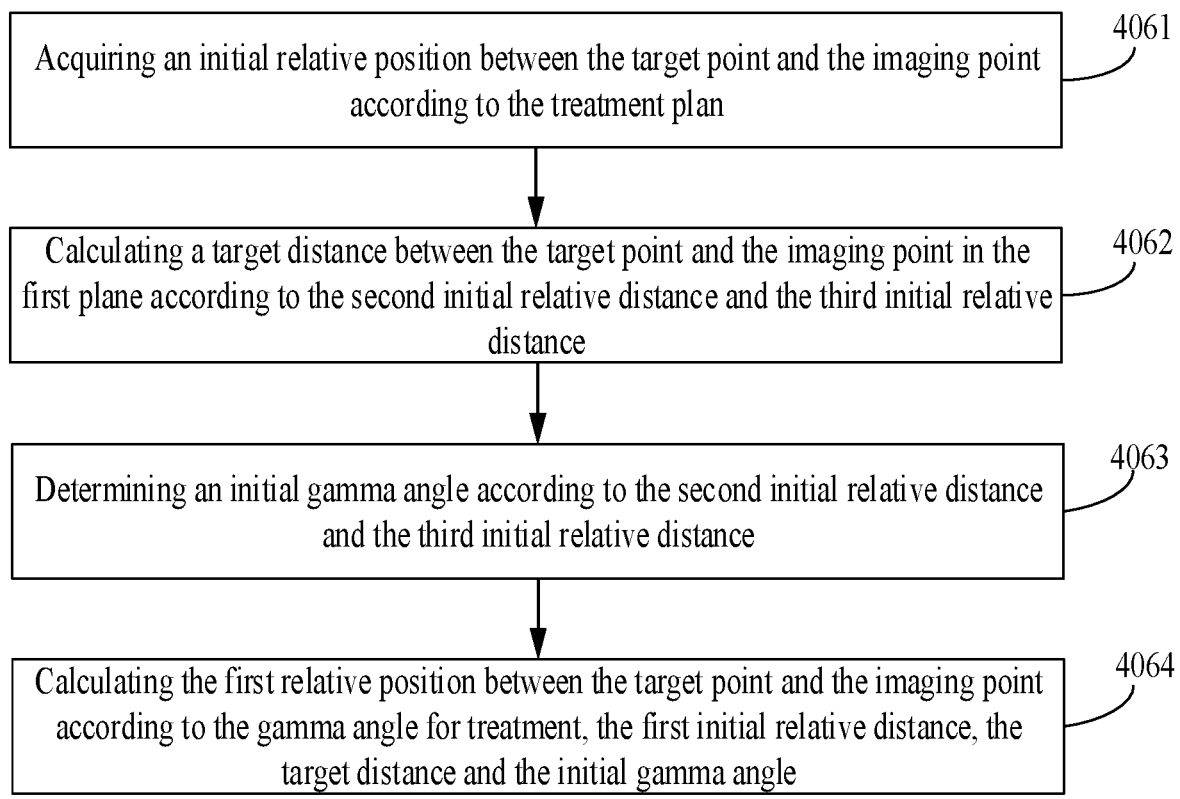
FIG. 6 is a flowchart of a method for determining a first relative position between a target point of an affected part and an imaging point according to the embodiment 1 of the present disclosure.

FIG. 6 is a flowchart of a method for determining a first relative position between a target point of an affected part and an imaging point according to the embodiment 1 of the present disclosure. As shown in FIG. 6, the method may include following steps.

In step 4061, an initial relative position between the target point and the imaging point is acquired according to the treatment plan.

In the embodiment 1 of the present disclosure, the target point A3 acquired by the host computer 02 is located in the image coordinate system, and the imaging point A1 is located in the coordinate system where the treatment couch 03 is located (also referred to as the equipment coordinate system). Thus, for the convenience of calculation, the host computer 02 may firstly convert positional coordinates of the acquired target point A3 into the coordinate system where the treatment couch 03 is located, so that the target point A3 and the imaging point A1 are located in the same coordinate system. With reference to FIG. 1 and FIG. 2, the equipment coordinate system may be a 3D coordinate system consisting of a first axis X extending in a width direction of the treatment couch 03, a second axis Y extending in a length direction of the treatment couch 03, and a third axis Z extending in a height direction of the treatment couch 03.

Correspondingly, the initial relative position may include a first initial relative distance TIx between the target point A3 and the imaging point A1 in the width direction of the treatment couch 03, a second initial relative distance TIy between the target point A3 and the imaging point A1 in the length direction of the treatment couch 03, and a third initial relative distance TIz between the target point A3 and the imaging point A1 in the height direction of the treatment couch 03. That is, the initial relative position between the target point A3 and the imaging point A1 may be expressed as (TIx, TIy, TIz).

For example, it is assumed that, after the host computer 02 converts the position of the acquired target point A3 into the equipment coordinate system, the coordinates of the target point A3 are (Xb, Yb, Zb), and the coordinates of the acquired imaging point A1 in the equipment coordinate system are (Xi, Yi, Zi). Then, the determined initial relative position (TIx, TIy, TIz) between the target point A3 and the imaging point A1 may satisfy: TIx=Xb−Xi, TIy=Yb−Yi, TIz=Zb−Zi.

In step 4062, the target distance between the target point and the imaging point in the first plane is calculated according to the second initial relative distance and the third initial relative distance.

The first plane may be a plane where the third axis Z extending in the length direction of the treatment couch and the second axis Y extending in the height direction of the treatment couch are located, i.e., the YOZ plane shown in FIG. 1.

Figure 7:
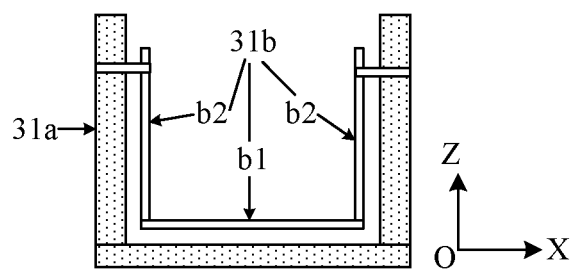
FIG. 7 is a schematically structural diagram of a gamma angle adjustment device according to the embodiment 1 of the present disclosure.
Figure 8:
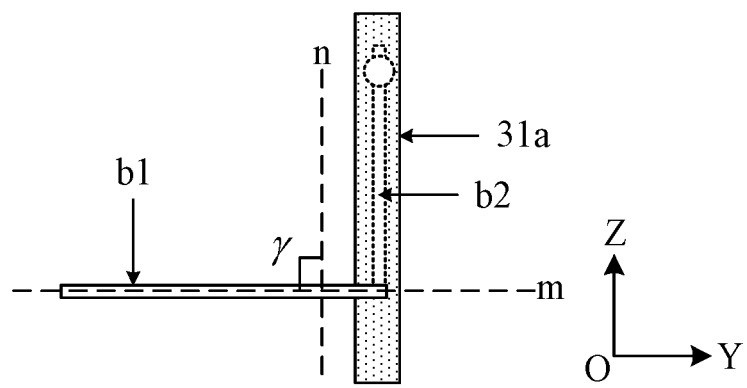
FIG. 8 is a side view of a gamma angle adjustment device according to the embodiment 1 of the present disclosure.
Figure 9:
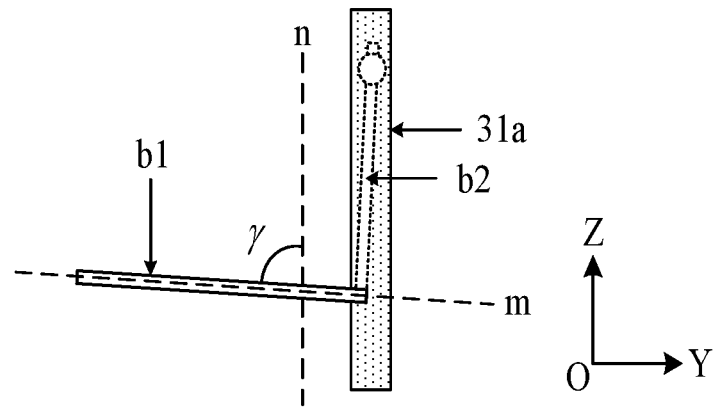
FIG. 9 is another side view of the gamma angle adjustment device according to the embodiment 1 of the present disclosure.

FIG. 7 is a schematically structural diagram of a gamma angle adjustment device according to the embodiment 1 of the present disclosure. As shown in FIG. 7, the gamma angle adjustment device 031 may include a fix frame 31a and a support frame 31b. The fix frame 31a may be fixed on the treatment couch 03, and the support frame 31b is rotatably connected to the fix frame 31a. FIG. 8 and FIG. 9 are side views of the gamma angle adjustment device 031 provided by the embodiment 1 of the present disclosure. With reference to FIG. 8 and FIG. 9, it may be seen that the support frame 31b may include a support panel b1 for supporting the affected part of the patient (such as, the head), and two connection rods b2 which are arranged oppositely. One end of each connection rod b2 is fixedly connected to the support panel b1, and the other end is rotatably connected to the fix frame 31a. Comparing FIG. 8 with FIG. 9, it may be seen that the connection rods b2 may drive the support panel b1 to rotate in the vertical plane (namely, the YOZ plane), thereby adjusting the gamma angle γ. The embodiment 1 of the present disclosure does not limit the specific structure of the gamma angle adjustment device 031, and only takes the structure shown in FIG. 7 to FIG. 9 as an example for illustration.

According to the aforesaid analysis, the gamma angle adjustment device 031 may only rotate in the first plane YOZ. That is, during the process of adjusting the gamma angle, the position of the target point A3 only changes in the first plane YOZ, and the coordinates of the target point A3 on the first axis X do not change. Thus, after calculating and obtaining the initial relative position (TIx, TIy, TIz), the host computer 02 may firstly calculate the target distance $L_{TI}$ between the target point A3 and the imaging point A1 in the first plane YOZ according to the second initial relative distance TIy and the third initial relative distance TIz. The target distance $L_{TI}$ may satisfy: $L_{TI}=\sqrt{(TIy)^2+(TIz)^2}$.

In step 4063, an initial gamma angle is determined according to the second initial relative distance and the third initial relative distance.

The host computer 02 may determine the initial gamma angle γ0 according to the second initial relative distance TIy and the third initial relative distance TIz. The process of determining the initial gamma angle γ0 may be implemented by the following logic:

```
If (TIy=0) {
  If (TIz>0) γ0 = 90°;
  Else γ0 = −90°;
} Else If (TIy>0) {
  γ0 = arctan(TIz/TIy); }
  Else {γ0 = arctan(TIz/TIy)+180°;
}
```

With reference to the aforesaid logic, it may be seen that the initial gamma angle γ0 may be determined to be 90° when the second initial relative distance TIy is equal to 0 and the third initial relative distance TIz is greater than 0.

The IGS system may determine that the initial gamma angle γ0 is negative 90° when the second initial relative distance TIy is equal to 0 and the third initial relative distance TIz is not greater than 0.

It may be determined that the initial gamma angle γ0 is an arctangent value of a ratio of the third initial relative distance TIz to the second initial relative distance TIy when the second initial relative distance TIy is greater than 0.

It may be determined that the initial gamma angle γ0 is a sum of 180° and the arctangent value of the ratio of the third initial relative distance TIz to the second initial relative distance TIy when the second initial relative distance TIy is not greater than 0.

In step 4064, the first relative position between the target point and the imaging point is calculated according to the gamma angle for treatment, the first initial relative distance, the target distance and the initial gamma angle.

In the embodiment 1 of the present disclosure, the first relative position may include, at the gamma angle r for treatment, a first relative distance TIxg between the target point A3 and the imaging point A1 in the width direction of the treatment couch 03, a second relative distance TIyg between the target point A3 and the imaging point A1 in the length direction of the treatment couch 03, and a third relative distance TIzg between the target point A3 and the imaging point A1 in the height direction of the treatment couch 03. Correspondingly, the first relative position (TIxg, TIyg, TIzg) calculated and obtained by the host computer 02 according to the acquired gamma angle for treatment, the first initial relative distance TIx, the target distance LTI and the initial gamma angle γ0 may satisfy:

$$TIxg=TIx \qquad \text{Formula (1);}$$

$$TIyg=L_{TI} \times \cos(\gamma 0+90°-\gamma) \qquad \text{Formula (2); and}$$

$$TIzg=L_{TI} \times \sin(\gamma 0+90°-\gamma) \qquad \text{Formula (3).}$$

With reference to the formula (1), since the position of the target point A3 only changes in the first plane YOZ during the process of adjusting the gamma angler, the coordinates of the target point A3 on the first axis X will not change. That is, there is no necessity to consider the relative distance between the target point A3 and the imaging point A1 on the first axis X. Thus, the first initial relative distance TIx may be directly determined as the first relative distance TIxg.

With reference to the formula (2), it may be seen that the product of the target distance $L_{TI}$ and the cosine value of the first angle α may be determined as the second relative distance TIyg.

The first angle α herein may be an angle obtained by adding the initial gamma angle γ0 to 90°, and then subtracting the gamma angle γ for treatment. That is, the first angle α may satisfy: α=γ0+90°−γ.

With reference to the formula (3), it may be seen that the product of the target distance $L_{TI}$ and the sine value of the first angle α may be determined as the third relative distance TIzg.

In step 407, the second relative position between the imaging point and the equipment isocenter is acquired.

The position of the equipment isocenter A2 is also fixed in the radiotherapy system. Thus, the host computer 02 may acquire the position of the equipment isocenter A2 directly. In addition, since the equipment isocenter A2 is also located in the equipment coordinate system, the host computer 02 may calculate and obtain the second relative position between the imaging point A1 and the equipment isocenter A2 directly according to the positional coordinates of the acquired imaging point A1 and the equipment isocenter A2.

The second relative position may include a first distance Xiso between the imaging point A1 and the equipment isocenter A2 in the width direction of the treatment couch 03, a second distance Yiso between the imaging point A1 and the equipment isocenter A2 in the length direction of the treatment couch 03, and a third distance Ziso between the imaging point A1 and the equipment isocenter A2 in the height direction of the treatment couch 03.

For example, the positional coordinates of the imaging point A1 acquired by the host computer 02 in the equipment coordinate system are (Xi, Yi, Zi), and the positional coordinates of the acquired equipment isocenter A2 in the equipment coordinate system are (Xc, Yc, Zc). Then, the host computer 02 may calculate and obtain the second relative position (Xiso, Yiso, Ziso) of the imaging point A1 and the isocenter point A2 of the device, which satisfies:

$$Xiso=Xi-Xc, Yiso=Yi-Yc, Ziso=Zi-Zc.$$

In step 408, when the target point coincides with the equipment isocenter, the second coordinates of the treatment couch at the gamma angle for treatment are calculated according to the first coordinates, the first relative position and the second relative position.

In the embodiment 1 of the present disclosure, the host computer 02 may add the first coordinates to the second relative position, and then subtract the first relative position to obtain the second coordinates of the treatment couch 03 at the gamma angle γ for treatment when the target point A3 coincides with the equipment isocenter A2. The second coordinates may also include a first dimensional coordinate Xt extending in the width direction of the treatment couch 03, a second dimensional coordinate Yt extending in the length direction of the treatment couch 03, and a third dimensional coordinate Zt extending in the width direction of the treatment couch 03. That is, the second coordinates may be expressed as (Xt, Yt, Zt), and the second coordinates (Xt, Yt, Zt) may satisfy:

$$Xt=X1+Xiso-TIxg \quad \text{Formula (4)};$$

$$Yt=Y1+Yiso-TIyg \quad \text{Formula (5); and}$$

$$Zt=Z1+Ziso-TIzg \quad \text{Formula (6)}.$$

With reference to the formula (4), it may be seen that the first dimensional coordinate Xt is obtained by adding the first dimensional coordinate X1 in the first coordinate to the first distance Xiso and then subtracting the first relative distance TIxg.

With reference to the formula (5), it may be seen that the second dimensional coordinate Yt is obtained by adding the second dimensional coordinate Y1 in the first coordinate to the second distance Yiso and then subtracting the second relative distance TIyg.

With reference to the formula (6), it may be seen that the third dimensional coordinate Zt is obtained by adding the third coordinate Z1 in the first coordinate to the third distance Z1 so and then subtracting the third relative distance TIzg.

In step 409, the position of the treatment couch is adjusted according to the second coordinates.

In the embodiment 1 of the present disclosure, the host computer 02 may accurately adjust the position of the treatment couch 03 according to the calculated and obtained second coordinates (Xt, Yt, Zt), which improves the accuracy of the alignment between the target point A3 and the equipment isocenter A2 at the gamma angle for treatment, and improves the accuracy of the radiotherapy.

For example, for further ensuring the accuracy of the calculated and obtained second coordinates (Xt, Yt, Zt), after a the position of the treatment couch 03 is adjusted and the image registration on the CT reconstructed image and the IGS image is performed (that is, after the step 404 is executed), when the preset shooting point A4 coincides with the imaging point A1, the host computer 02 may further acquire a rotation angle at which the target point A3 rotates around the gamma angle rotation axis, according to a registration situation where the CT reconstruction image is registered with the IGS image. That is, when the preset shooting point A4 coincides with the imaging point A1, the rotation angle at which the patient's head rotates around the gamma angle rotation axis is determined. The gamma angle rotation axis herein is a rotation axis for adjusting the gamma angle in the gamma angle adjustment device 031.

The rotation angle may include a first angle θx rotating around a first axis X extending in a width direction of the treatment couch 03, a second angle θy rotating around a second axis Y extending in a length direction of the treatment couch 03, and a third angle θz rotating around a third axis Z extending in a height direction of the treatment couch 03. Further, the IGS system 01 may correct the first relative position (TIxg, TIyg, TIzg) according to the acquired rotation angle (θx, θy, θz).

For example, it is assumed that the target point A3 rotates around respective rotation axes in the following sequence: rotating θz around the third axis Z firstly, then rotating θy around the second axis Y, and finally rotating θx around the first axis X. That is, the sequence of respective rotation axes around which the patient's head rotates is Z, Y, and X. Thus, the corrected first relative position (Tx, Ty, Tz) obtained by correcting the first relative position (TIxg, TIyg, TIzg) according to the rotation angle (θx, θy, θz) may satisfy:

$$\begin{bmatrix} Tx \\ Ty \\ Tz \end{bmatrix} = \begin{bmatrix} 1 & 0 & 0 \\ 0 & \cos\theta x & -\sin\theta x \\ 0 & \sin\theta x & \cos\theta x \end{bmatrix} \begin{bmatrix} \cos\theta y & 0 & \sin\theta y \\ 0 & 1 & 0 \\ -\sin\theta y & 0 & \cos\theta y \end{bmatrix} \begin{bmatrix} \cos\theta z & -\sin\theta z & 0 \\ \sin\theta z & \cos\theta z & 0 \\ 0 & 0 & 1 \end{bmatrix} \begin{bmatrix} TIxg \\ TIyg \\ TIzg \end{bmatrix}.$$

It should be noted that if the sequence of respective gamma angle rotation axes around which the target point A3 rotates changes, the arrangement sequence of the matrices in the aforesaid correction formula shall be changed accordingly when correcting the first relative position (TIxg, TIyg, TIzg) according to the rotation angle (θx, θy, θz).

Correspondingly, the step 408 may be that when the target point A3 coincides with the equipment isocenter A2, the second coordinates (Xt, Yt, Zt) of the treatment couch 03 at the gamma angle γ for treatment are calculated according to the first coordinates (X1, Y1, Z1), the corrected first relative position (Tx, Ty, Tz) and the second relative position (Xiso, Yiso, Ziso). That is, the first dimensional coordinate Xt in the second coordinate of the treatment couch 03 may satisfy: Xt=X1+Xiso-Tx; the second coordinate Yt in the second coordinate of the treatment couch 03 may satisfy: Yt=Y1+Yiso-Ty, and the third coordinate Zt in the second coordinate of the treatment the 03 may satisfy: Zt=Z1+Ziso-Tz.

Optionally, the sequence of the steps of the positioning method provided by the embodiment 1 of the present disclosure may be appropriately adjusted, and the steps may also be added or deleted accordingly according to the situation. For example, the steps 401 to 405 may be executed after the step 407. That is, the first relative position between the target point of the affected part and the imaging point may be determined according to the gamma angle for treatment firstly, and the second relative position of the imaging point and the equipment isocenter may be acquired firstly and then acquiring the first coordinates. Any method that can be easily conceived by any one skilled in the art within the technical scope disclosed in the present disclosure shall be contained within the protection scope of the present disclosure, and therefore will not be described again.

In summary, the embodiment 1 of the present disclosure provides a positioning method. According to the method, when the target point coincides with the equipment isocenter, the second coordinates of the treatment couch at the gamma angle for treatment can be calculated according to the first coordinates of the treatment couch acquired when the preset shooting point coincides with the imaging point, the first relative position between the target point of the affected part and the imaging point, and the second relative position between the imaging point and the equipment isocenter. Then, the position of the treatment couch can be adjusted according to the second coordinates. Therefore, after adjusting the gamma angle during the radiotherapy, the second coordinates of the treatment couch at the adjusted gamma angle when the target point coincides with the equipment isocenter can be accurately calculated and obtained, which improves the accuracy of the alignment between the target point and the equipment isocenter at different gamma angles and improves the accuracy of the radiotherapy.

Figure 10:
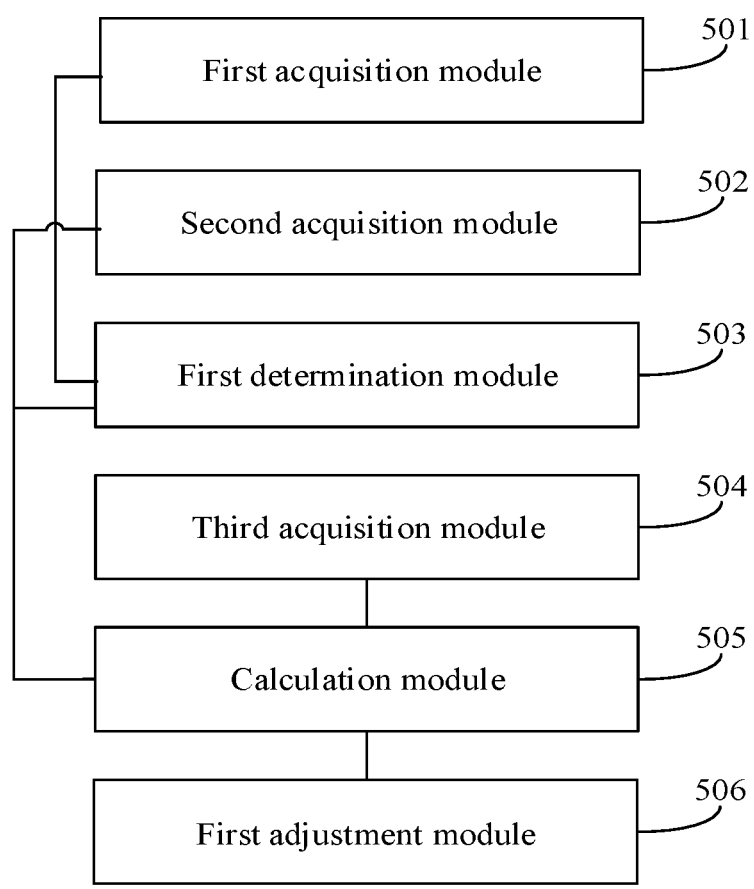
FIG. 10 is a block diagram of a positioning apparatus according to the embodiment 1 of the present disclosure.

FIG. 10 is a block diagram of a positioning apparatus according to the embodiment 1 of the present disclosure. The apparatus may be applied into the host computer 02 shown in FIG. 2. Alternatively, with reference to above description, the positioning apparatus may also be applied to the IGS system 01 or the treatment couch 03 shown in FIG. 1, which is not limited in the embodiment 1 of the present disclosure. The following embodiment 1 is illustrated by taking the positioning apparatus applied to the host computer 02 as an example. As shown in FIG. 10, the apparatus may include following modules.

A first acquisition module 501 is configured to acquire a gamma angle for treatment.

A second acquisition module 502 is configured to acquire first coordinates of a treatment couch, and the first coordinates are coordinates of the treatment couch when a preset shooting point coincides with an imaging point of an image guidance system IGS.

A first determination module 503 is configured to determine a first relative position between a target point of an affected part and the imaging point according to the gamma angle for treatment.

A third acquisition module 504 is configured to acquire a second relative position between the imaging point and an equipment isocenter.

A calculation module 505 is configured to calculate second coordinates of the treatment couch at the gamma angle for treatment when the target point coincides with the equipment isocenter according to the first coordinates, the first relative position and the second relative position.

A first adjustment module 506 is configured to adjust a position of the treatment couch according to the second coordinates.

In summary, the embodiment 1 of the present disclosure provides a positioning apparatus. In the apparatus, the calculation module can calculate the second coordinates of the treatment couch at the gamma angle for treatment when the target point coincides with the equipment isocenter according to the first coordinates of the treatment couch acquired by the second acquisition module when the preset shooting point coincides with the imaging point, the first relative position between the target point of the affected part and the imaging point determined by the first determination module, and the second relative position between the imaging point and the equipment isocenter acquired by the third acquisition module. Then, the adjustment module can adjust the position of the treatment couch according to the second coordinates. Therefore, after adjusting the gamma angle during the radiotherapy, the second coordinates of the treatment couch at the adjusted gamma angle when the target point coincides with the equipment isocenter can be accurately calculated, which improves the accuracy of the alignment between the target point and the equipment isocenter at different gamma angles and improves the accuracy of the radiotherapy.

Figure 11:
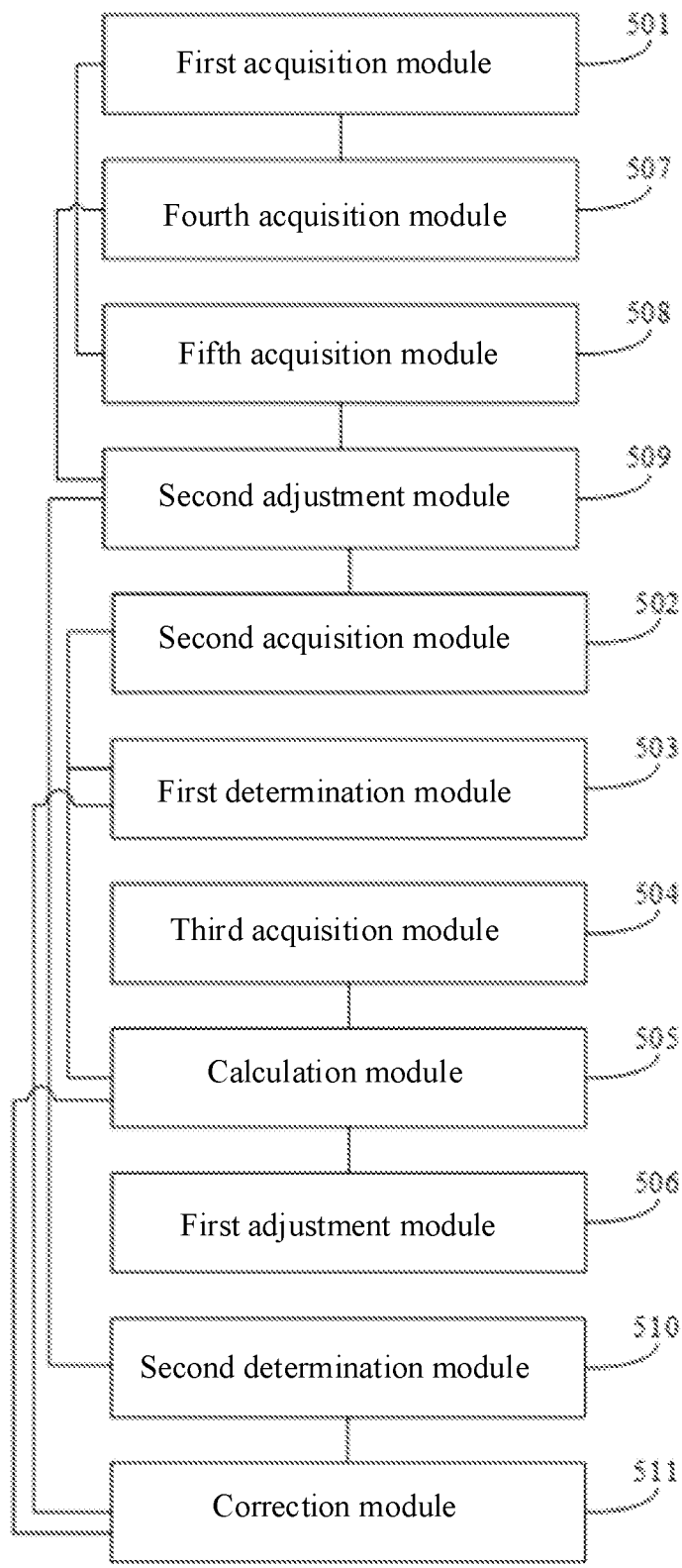
FIG. 11 is a block diagram of another positioning apparatus according to the embodiment 1 of the present disclosure.

FIG. 11 is a block diagram of another positioning apparatus according to the embodiment 1 of the present disclosure. The apparatus may be applied into the host computer 02 shown in FIG. 2. Alternatively, with reference to above description, the positioning apparatus may also be applied to the IGS system 01 or the treatment couch 03 shown in FIG. 1, which is not limited in the embodiment 1 of the present disclosure. The following embodiment 1 is illustrated by taking the positioning apparatus applied to the host computer 02 as an example. As shown in FIG. 11, the apparatus may further include following modules.

A fourth acquisition module 507 is configured to acquire a reconstructed image of the gamma angle for treatment before acquiring the first coordinates of the treatment couch, and the reconstructed image is an image reconstructed from an electronic image of the affected part acquired in advance.

A fifth acquisition module 508 is configured to acquire an IGS image of the affected part at the gamma angle for treatment, and the IGS image is an image generated by the IGS.

A second adjustment module 509 is configured to perform an image registration on the reconstructed image and the IGS image by adjusting the position of the treatment couch, so that the preset shooting point coincides with the imaging point.

Optionally, with reference to FIG. 11, the apparatus may further include following modules.

A second determination module 510 is configured to determine, after performing the image registration on the reconstructed image and the IGS image by adjusting the position of the treatment couch, a rotation angle at which the target point rotates around a rotation axis, when the preset shooting point coincides with the imaging point. The rotation angle may include a first angle rotating around a first axis extending in a width direction of the treatment couch, a second angle rotating around a second axis extending in a length direction of the treatment couch, and a third angle rotating around a third axis extending in a height direction of the treatment couch.

A correction module 511 is configured to correct the first relative position according to the rotation angle.

Correspondingly, a calculation module 505 may be configured to calculate the second coordinates of the treatment couch at the gamma angle for treatment when the target point coincides with the equipment isocenter, according to the first coordinates, a corrected first relative position and the second relative position.

Figure 12:
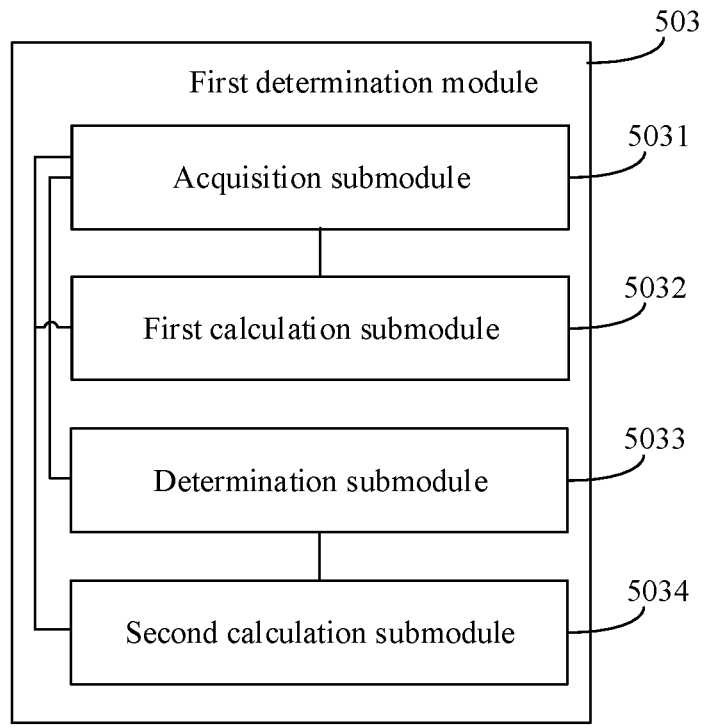
FIG. 12 is a block diagram of a first determination module according to the embodiment 1 of the present disclosure.

FIG. 12 is a block diagram of the first determination module 503 according to the embodiment 1 of the present disclosure. As shown in FIG. 12, the first determination module 503 may further include following submodules.

An acquisition submodule 5031 is configured to acquire an initial relative position between the target point and the imaging point according to the treatment plan. The initial relative position may include a first initial relative distance between the target point and the imaging point in a width direction of the treatment couch, a second initial relative distance between the target point and the imaging point in a length direction of the treatment couch, and a third initial relative distance between the target point and the imaging point in a height direction of the treatment couch.

A first calculation submodule 5032 is configured to calculate a target distance between the target point and the imaging point in a first plane according to the second initial relative distance and the third initial relative distance. The first plane is a plane where the first axis extending in the length direction of the treatment couch and the second axis extending in the height direction of the treatment couch are located.

A determination submodule 5033 is configured to determine an initial gamma angle according to the second initial relative distance and the third initial relative distance.

A second calculation submodule 5034 is configured to calculate a first relative position between the target point and the imaging point according to the gamma angle for treatment, the first initial relative distance, the target distance and the initial gamma angle.

Optionally, in the embodiment 1 of the present disclosure, the determination submodule 5033 may be configured to:

determine that the initial gamma angle is 90° when the second initial relative distance is equal to 0 and the third initial relative distance is greater than 0;

determine that the initial gamma angle is negative 90° when the second initial relative distance is equal to 0 and the third initial relative distance is not greater than 0;

determine that the initial gamma angle is an arctangent value of a ratio of the third initial relative distance to the second initial relative distance when the second initial relative distance is greater than 0; and determine that the initial gamma angle is a sum of 180° and the arctangent value of the ratio of the third initial relative distance to the second initial relative distance when the second initial relative distance is not greater than 0.

In the embodiment 1 of the present disclosure, the first relative position may include, at the gamma angle for treatment, a first relative distance between the target point and the imaging point in a width direction of the treatment couch, a second relative distance between the target point and the imaging point in a length direction of the treatment couch, and a third relative distance between the target point and the imaging point in a height direction of the treatment couch.

Optionally, the second calculation submodule 5034 is configured to:

determine the first initial relative distance as the first relative distance;

determine a product of the target distance and a cosine value of a first angle as the second relative distance, and the first angle is an angle obtained by adding the initial gamma angle to 90° and then subtracting the gamma angle for treatment; and determine the product of the target distance and a sine value of the first angle as the third relative distance.

Optionally, the calculation module is configured to obtain the second coordinates of the treatment couch by adding the first coordinates to the second relative position and then subtracting the first relative position.

In summary, the embodiment 1 of the present disclosure provides a positioning apparatus. In the apparatus, the calculation module can calculate the second coordinates of the treatment couch at the gamma angle for treatment when the target point coincides with the equipment isocenter according to the first coordinates of the treatment couch acquired by the second acquisition module when the preset shooting point coincides with the imaging point, the first relative position between the target point of the affected part and the imaging point determined by the first determination module, and the second relative position between the imaging point and the equipment isocenter acquired by the third acquisition module. Then, the adjustment module can adjust the position of the treatment couch according to the second coordinates. Therefore, after adjusting the gamma angle during the radiotherapy, the second coordinates of the treatment couch at the adjusted gamma angle when the target point coincides with the equipment isocenter can be accurately calculated, which improves the accuracy of the alignment between the target point and the equipment isocenter at different gamma angles and improves the accuracy of the radiotherapy.

With regard to the positioning apparatus in the forgoing described embodiments, the specific manner in which the respective modules perform the operations has been described in detail in the embodiments of the method, and will not be explained in detail herein.

The embodiment 1 of the present disclosure provides a positioning apparatus. The positioning apparatus may include a processor and a memory in which instructions are stored, and the instructions may be loaded and executed by the processor to implement the positioning method shown in any one of FIGS. 3, 4, and 6.

Furthermore, the embodiment 1 of the present disclosure provides a storage medium in which instructions are stored. When the storage medium runs at a processing component, the processing component is actuated to execute the positioning method shown in any one of FIGS. 3, 4, and 6.

The embodiment 1 of the present disclosure may further provide a radiotherapy system, which includes a positioning apparatus shown in any one of FIG. 10 and FIG. 11.

Embodiment 2

Figure 13:
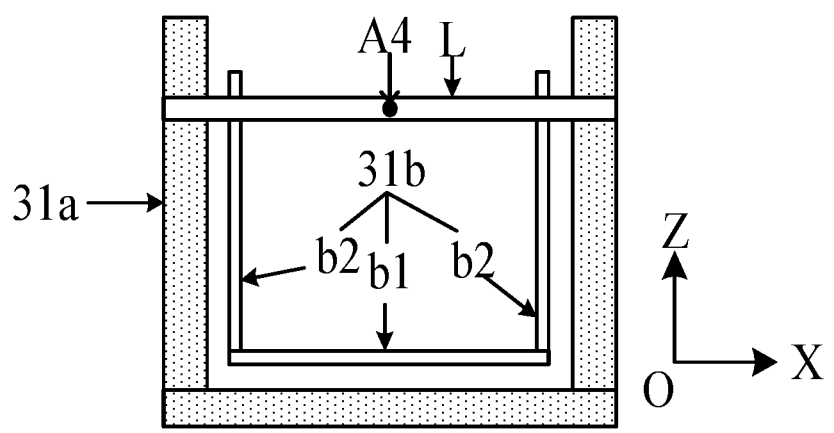
FIG. 13 is a front view of a gamma angle adjustment device according to an embodiment 2 of the present disclosure.

FIG. 13 is a front view of a gamma angle adjustment device 031 according to an embodiment 2 of the present disclosure. According to FIG. 13, it can be seen that the gamma angle adjustment device 031 may include a fix frame 31a and a support frame 31b. The fix frame 31a may be fixed on the treatment couch 03, and the support frame 31b is rotatably connected to the fix frame 31a. For example, an axis Las shown in FIG. 13 may be a gamma angle rotation axis. Accordingly, an A4 may be a gamma angle rotation axis central point of the gamma angle rotation axis L. The embodiment 2 of the present disclosure does not limit the specific structure of the gamma angle adjustment device 031, and only takes the structure shown in FIG. 13 as an example for illustration.

The embodiment 2 of the present disclosure provides a positioning method realized by a computer, which is capable of calculating coordinates of the treatment couch 03 at different gamma angles when the target point A3 coincides with the equipment isocenter A2. In this way, even after the gamma angle changes, the host computer 02 can also accurately adjust position of the treatment couch 03 according to the calculated coordinates of the treatment couch 03, which improves the accuracy of the alignment between the target point A3 and the equipment isocenter A2 and further improves the accuracy of the radiotherapy.

Figure 14:
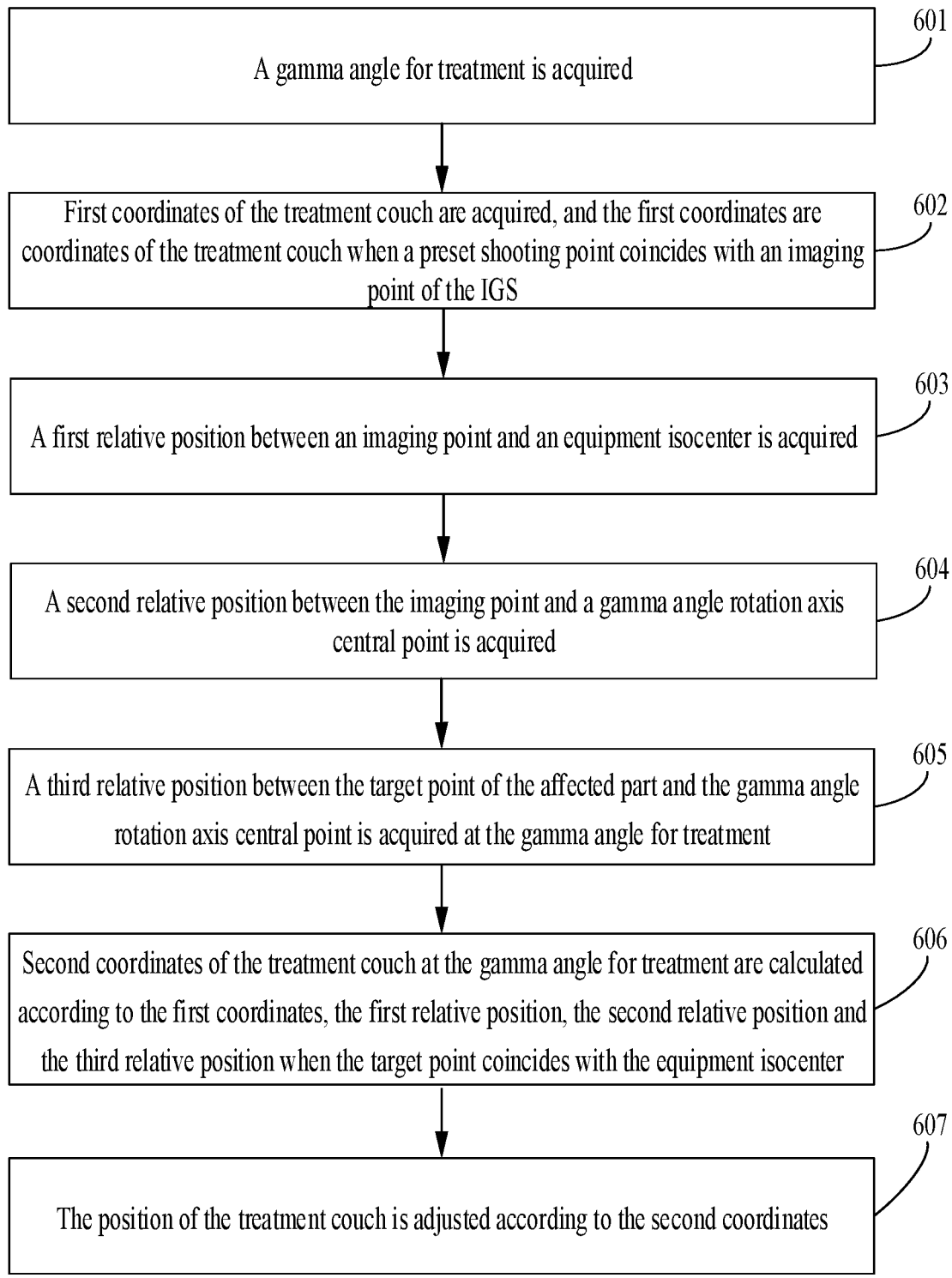
FIG. 14 is a flowchart of a positioning method according to the embodiment 2 of the present disclosure.

FIG. 14 is a flowchart of a positioning method according to the embodiment 2 of the present disclosure. The positioning method may be applied to the host computer 02 shown in FIG. 1. As shown in FIG. 14, the method may include following steps.

In step 601, a gamma angle for treatment is acquired.

In the embodiment 2 of the present disclosure, the gamma angle for treatment may be a current gamma angle for treatment.

For example, the therapist may fix the patient at a certain gamma angle through the gamma angle adjustment device 031 and input the current gamma angle to the host computer 02. That is, the host computer 02 may acquire the gamma angle γ for treatment input by the therapist. Alternatively, when the therapist fixes the patient at a certain gamma angle through the gamma angle adjustment device 031, the host computer 02 may detect the gamma angle γ for treatment automatically. Further alternatively, the host computer 02 may determine the gamma angle γ for treatment according to the treatment plan acquired in advance. The embodiment 2 of the present disclosure does not limit the manner in which the host computer 02 acquires the gamma angle for treatment.

In step 302, first coordinates of the treatment couch are acquired. The first coordinates are coordinates of the treatment couch when a preset shooting point coincides with an imaging point of the IGS.

For example, the host computer 02 may acquire the CT reconstructed image at the gamma angle for treatment. The CT reconstructed image may be an image, which is reconstructed by the IGS system 01 according to an electronic image of the affected part acquired in advance, that is, an image of the patient before the treatment such as a CT image, and is sent to the host computer 02. The CT reconstructed image may include the preset shooting point. Then, when the host computer 02 drives the treatment couch 03 to send the affected part of the patient into the imaging area (i.e., the shooting area), the IGS system 01 may obtain the IGS image of the affected part of the patient and send the acquired IGS image to the host computer 02.

In order to determine whether the preset shooting point coincides with the imaging point A1, the host computer 02 may perform image registration on the acquired IGS image and the CT reconstructed image, and continuously adjust the position of the treatment couch 03 during the registration process, so as to finally enable the preset shooting point to coincide with the imaging point A1. When the preset shooting point coincides with the imaging point, the host computer 02 may acquire the first coordinates of the treatment couch 03 at this point.

In step 303, a first relative position between an imaging point and an equipment isocenter is acquired.

Since the positions of the imaging point A1 and the equipment isocenter A2 remain constant in the radiotherapy system and both the imaging point A1 and the equipment isocenter A2 are located in the coordinate system where the treatment couch 03 is located (the coordinate system may also be called as the equipment coordinate system), the IGS system 01 may acquire the position coordinates of the imaging point A1 and the equipment isocenter A2 directly and may calculate a first relative position between the imaging point A1 and the equipment isocenter A2 according to the acquired position coordinates of the imaging point A1 and the equipment isocenter A2.

In step 304, a second relative position between the imaging point and a gamma angle rotation axis central point is acquired.

In the embodiment 2 of the present disclosure, the gamma angle rotation axis central point A4 may be a central point of the gamma angle rotation axis L of the gamma angle adjustment device 031 which is used for adjusting a gamma angle. Since the position of the gamma angle rotation axis central point A4 also remains constant and the gamma angle rotation axis central point A4 is also located in the equipment coordinate system, the IGS system 01 may acquire the position coordinate of the gamma angle rotation axis central point A4 directly and may calculate a second relative position between the imaging point A1 and the gamma angle rotation axis central point A4 according to the acquired position coordinates of the imaging point A1 and the gamma angle rotation axis central point A4.

In step 305, a third relative position between the target point of the affected part and the gamma angle rotation axis central point is acquired at the gamma angle for treatment.

In the embodiment 2 of the present disclosure, the position of the target point A3 of the affected part at the gamma angle for treatment may be determined according to the treatment plan.

For example, before the radiotherapy, the host computer 02 may acquire the CT reconstructed image at different gamma angles for treatment. According to the CT reconstructed image, the therapist may formulate a treatment plan for the patient including the position of the target point A3 and input the treatment plan to the host computer 02, so that the host computer 02 may acquire the position of the target point A3 from the treatment plan. Since the target point A3 and the gamma angle rotation axis central point A4 are located in different coordinate systems, the host computer 02 may also convert the positions of the target point A3 and the gamma angle rotation axis central point A4 into a same coordinate system to calculate the third relative position between the target point A3 and the gamma angle rotation axis central point A4.

In step 306, when the target point coincides with the equipment isocenter, second coordinates of the treatment couch at the gamma angle for treatment are calculated according to the first coordinates, the first relative position, the second relative position, and the third relative position.

After acquiring the first coordinates, the first relative position, the second relative position and the third relative position, the host computer 02 may accurately calculate and obtain the second coordinates of the treatment couch at the gamma angle for treatment when the target point coincides with the equipment isocenter according to the first coordinates, the first relative position, the second relative position and the third relative position.

In step 307, the position of the treatment couch is adjusted according to the second coordinates.

Furthermore, the host computer 02 may accurately adjust the position of the treatment couch 03 according to the calculated second coordinates, which improves the accuracy of the alignment between the target point A3 and the equipment isocenter A2 at the gamma angle for treatment, thereby improving the accuracy of the radiotherapy.

In summary, the embodiment 2 of the present disclosure provides a positioning method realized by a computer. According to the method, when the target point coincides with the equipment isocenter, the second coordinates of the treatment couch at the gamma angle for treatment can be calculated according to the first coordinates of the treatment couch acquired when the preset shooting point coincides with the imaging point, the first relative position between the imaging point and the equipment isocenter, the second relative position between the imaging point and the gamma angle rotation axis central point, and the third relative position between the target point of the affected part and the gamma angle rotation axis central point. Then, the position of the treatment couch can be adjusted according to the second coordinates. Therefore, after adjusting the gamma angle during the radiotherapy, the second coordinates of the treatment couch at the adjusted gamma angle can be accurately calculated when the target point coincides with the equipment isocenter, which improves the accuracy of the alignment between the target point and the equipment isocenter at different gamma angles and improves the accuracy of the radiotherapy.

It should be noted that the embodiment 2 of the present disclosure is illustrated by taking an example where the host computer 02 has a communication connection with the IGS system 01 and the treatment couch 03 and the steps 601 to 607 are executed through the host computer 02. During the actual execution process, the treatment couch 03 and the IGS system 01 may be respectively provided with processors, and the treatment couch 03 and the IGS system 01 may execute the corresponding steps in the aforesaid embodiment 2 through their respective processors correspondingly, which is not limited in the embodiment 2 of the present disclosure. Only FIG. 14 and the aforesaid embodiment 2 are taken as examples for illustration herein.

Figure 15:
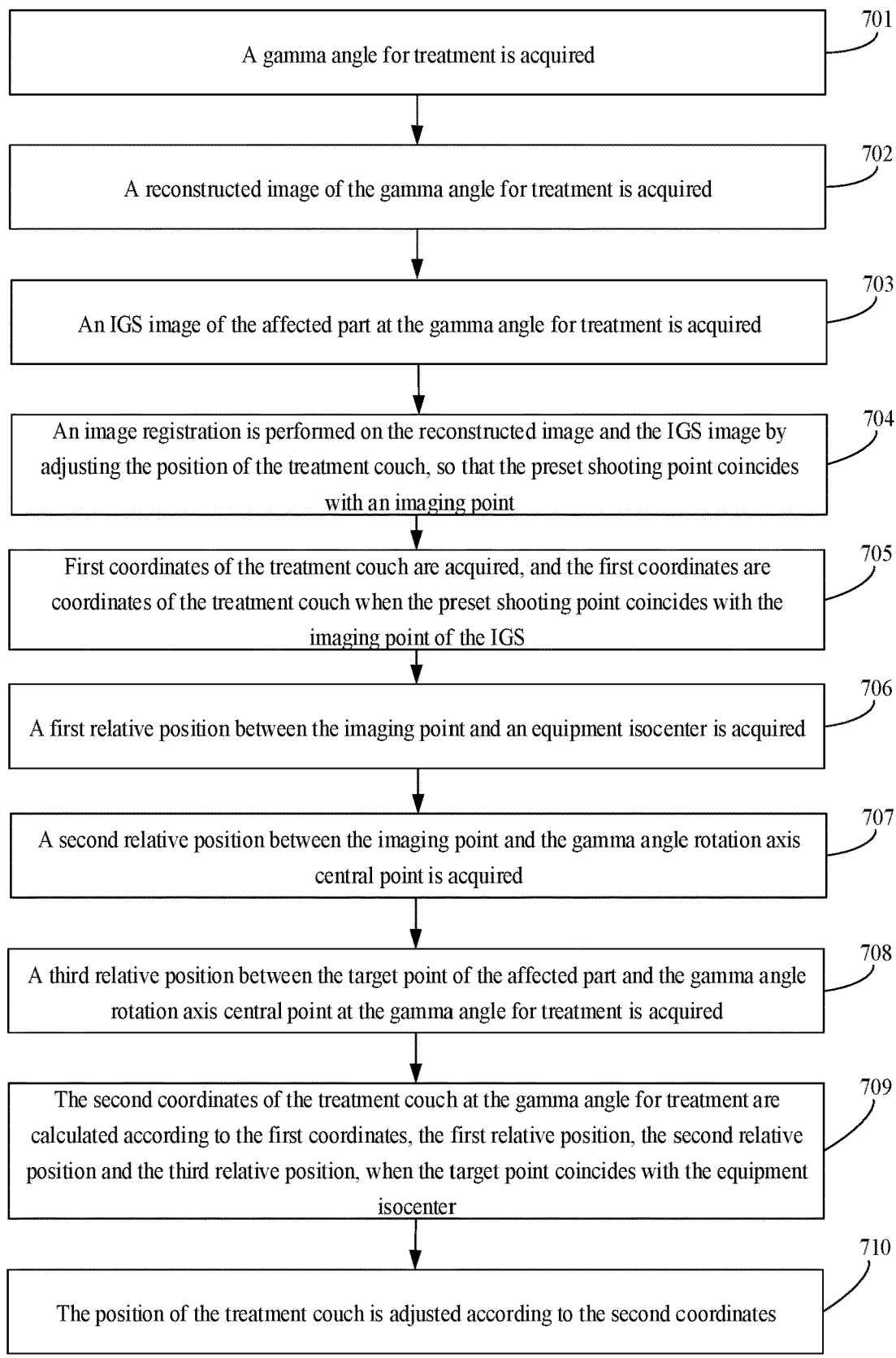
FIG. 15 is a flowchart of another positioning method according to the embodiment 2 of the present disclosure.

FIG. 15 is a flowchart of another positioning method realized by a computer according to the embodiment 2 of the present disclosure. The positioning method may be applied to the host computer 02 shown in FIG. 1. Alternatively, with reference to above description, the positioning method may also be applied to the IGS system 01 or the treatment couch 03 shown in FIG. 1, which is not limited in the embodiment 2 of the present disclosure. The following embodiment is illustrated by taking the positioning method applied to the host computer 02 as an example. As shown in FIG. 15, the method may include following steps.

In step 701, a gamma angle for treatment is acquired.

In the embodiment 2 of the present disclosure, the gamma angle for treatment may be a current gamma angle for treatment.

For example, as an example implementation, the therapist may fix the patient at a certain gamma angle through the gamma angle adjustment device 031 and input the current gamma angle γ to the host computer 02. That is, the host computer 02 may acquire the gamma angle γ for treatment input by the therapist. Such an acquiring method is relatively reliable.

As another implementation, when the therapist fixes the patient at a certain gamma angle γ through the gamma angle adjustment device 031, the host computer 02 may detect the gamma angle γ for treatment automatically. Such an acquiring method is relatively efficient.

As still another implementation, the host computer 02 may determine the gamma angle 7 for treatment according to the treatment plan acquired in advance.

For example, assuming that the current gamma angle γ for treatment is 70°, the therapist may adjust the gamma angle γ to be 70° by adjusting the gamma angle adjustment device 031 shown in FIG. 1. After completing the fixing of the gamma angle adjustment device 031, the therapist may input the gamma angle γ for treatment to the host computer 02 as γ=70°, and then the gamma angle γ for treatment acquired by the host computer 02 is 70°.

In step 702, a reconstructed image of the gamma angle for treatment is acquired.

In the embodiment 2 of the present disclosure, the reconstructed image may be an image reconstructed from an electronic image (such as, a CT image) of the affected part acquired in advance. The reconstructed image may be an image reconstructed by the IGS system 01 according to the electronic image. Alternatively, the reconstructed image may be an image reconstructed by an electronic image generation device (for example, a CT device) according to the electronic image. Further alternatively, the reconstructed image may be a reconstructed image generated by other image processing systems according to the electronic image. The embodiment 2 of the present disclosure does not limit the device that generates the reconstructed image.

Figure 16:
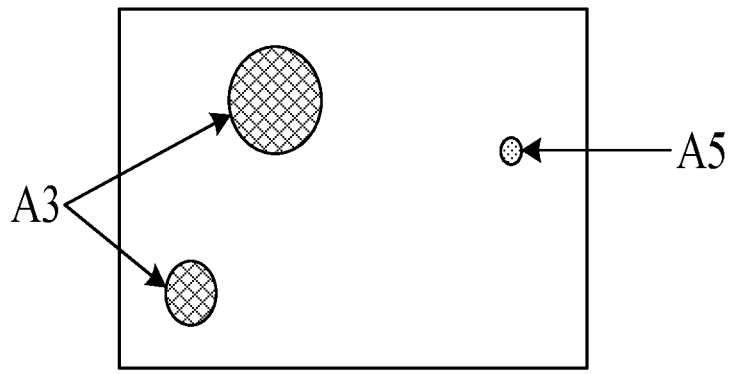
FIG. 16 is a schematic diagram of an acquired CT reconstructed image including a target point and a preset shooting point according to the embodiment 2 of the present disclosure.

For example, the reconstructed image may be a digitally reconstructed radiological image (DRR image), and the DRR image may be an image reconstructed by the IGS system 01 according to the CT image after acquiring the CT image of the affected part. Correspondingly, the reconstructed image may also be referred to as a CT-DRR film. With reference to FIG. 16, the CT-DRR film may include positions of the target point A3 and the preset shooting point A5. FIG. 16 shows the CT-DRR film including two target points A3.

For example, the electronic image acquired by the IGS system 01 may be a plurality of continuous tomographic images acquired by scanning the affected part with a CT device. That is, the electronic image may be a group of image sequences. Each tomographic image in the image sequence is perpendicular to the horizontal axis of the treatment couch 03, and an extension direction of the horizontal axis may be parallel to a movement direction (that is, a forward direction) of the treatment couch 03 while moving close to a treatment chamber. Since each tomographic image is a two dimensional image, the plurality of continuous tomographic images may be reconstructed as three dimensional (3D) volume data of the affected part through computer processing. For example, the layer thickness of the CT device may be no more than 2 mm when scanning the affected part, and there is no interlayer spacing.

During the process of image reconstruction, the IGS system 01 may determine the rotation axis firstly according to the preset shooting point A5 in the CT image. The rotation axis may be a designated coordinate axis of the coordinate system where the shooting point A5 is located, or a linear axis parallel to the designated coordinate axis. For example, the linear axis passing through the shooting point A5 and parallel to the designated coordinate axis (such as, the X axis) in the coordinate system where the shooting point A5 is located may be determined as the rotation axis. Furthermore, for each gamma angle, the IGS system 01 may rotate the CT image by a deflection angle by taking the rotation axis as the axis to reconstruct the reconstructed image of the gamma angle. The deflection angle is a deflection angle between the gamma angle and an initial gamma angle when the electronic image is collected. Specifically, the IGS system 01 may rotate the 3D volume data corresponding to the plurality of tomographic images by the deflection angle by taking the rotation axis as the axis, and project the rotated 3D volume data on a virtual imaging surface of the IGS system 01 according to installation parameters of the IGS system 01, thereby obtaining the reconstructed image of the gamma angle.

The shooting point A5 in the CT image is a preset point in the CT image, and the position of the shooting point A5 may be described by coordinates of the three coordinate axes in the 3D coordinate system where the shooting point A5 is located. The virtual imaging surface is an imaging surface of the IGS system 01 constructed virtually in the coordinate system where the shooting point A5 is located. The position of the virtual imaging surface in the 3D coordinate system where the shooting point A5 is located is the same as the position of the imaging surface of the detector of the IGS system 01 in the coordinate system (also referred to as an equipment coordinate system) where the treatment couch 03 is located.

For example, as described above, the IGS system 01 may include multiple groups of image collection components, and each group of image collection components may include a detector 011 and a tube 012 that are disposed opposite to each other. The installation parameters of each group of the image collection components may affect the virtual imaging surface when the IGS system 01 generates the reconstructed image. Thus, prior to projecting the rotated 3D volume data on the virtual imaging surface of the IGS system 01, the IGS system 01 may determine the position of the virtual imaging surface of the IGS system 01 in the coordinate system where the shooting point is located according to the installation parameters of the image collection components. The installation parameters may include: an angle between the rays of two groups of image collection components, a distance between the detector 011 and the tube 012 in each group of the image collection components, and a distance between an intersection of the rays and the detector 011, and the like. The rays of each group of the image collection components may be a connection line between the detector 011 and the tube 012 in the group of image collection components, and the imaging surface of the detector 011 is perpendicular to the rays emitted by the tube 012.

It should be noted that: when rotating the 3D volume data to reconstruct the reconstructed image of a certain gamma angle, the rotation direction of the 3D volume data may be determined according to the deflection direction of the gamma angle relative to the initial gamma angle when the CT image is acquired, so as to ensure that the rotation direction of the 3D volume data in the image coordinate system is consistent with the deflection direction of the gamma angle in the coordinate system where the treatment couch 03 is located, and the deflection angles are also consistent.

Furthermore, the IGS system 01 may send the reconstructed CT-DRR films of the plurality of gamma angles to the host computer 02. After acquiring the gamma angle for treatment, the host computer 02 may take the reconstructed image of the gamma angle for treatment from the reconstructed image of at least one gamma angle.

For example, the host computer 02 may take the reconstructed image of the gamma angle γ for treatment from the plurality of reconstructed images received in advance after acquiring the current gamma angle for treatment. For example, the IGS system 01 may reconstruct the reconstructed images at angles of 60°, 70°, 80°, 90°, 100°, and 110° according to the CT image, and send all the reconstructed images corresponding to the plurality of gamma angles to the host computer 02. The host computer 02 may take the reconstructed image at the gamma angle of 70° directly if the current gamma angle γ for treatment as acquired is 70°.

In step 703, an IGS image of the affected part at the gamma angle for treatment is acquired.

The IGS image is an image generated by the image guidance system 01 (i.e., IGS system 01). The host computer 02 may adjust the position of the treatment couch 03 according to the fixed coordinate values set in advance, and send the affected part of the patient into the imaging area of the IGS system. Since the current patient has been fixed at the gamma angle for treatment, the IGS system 01 may acquire the IGS image of the affected part at the gamma angle γ for treatment directly through the multiple groups of image collection components, and send the acquired IGS image to the host computer 02.

For example, the host computer 02 may send imaging instructions to the IGS system 01, and the IGS system 01 may control the two tubes 012 shown in FIG. 2 to emit rays after receiving the imaging instructions. Correspondingly, the two detectors 011 shown in FIG. 2 may both receive the rays emitted by the tubes 012, and the IGS system 01 may generate the IGS image according to the rays received by each detector 011 and send the IGS image to the host computer 02.

In step 704, an image registration is performed on the reconstructed image and the IGS image by adjusting the position of the treatment couch, so that the preset shooting point coincides with an imaging point.

In the embodiment 2 of the present disclosure, in order to determine whether the preset shooting point A5 in the reconstructed image (i.e., CT-DRR film) coincides with the imaging point A1, the host computer 02 may perform an image registration on the CT-DRR film and the IGS image, and continuously adjust the position of the treatment couch 03 during the image registration process, so as to finally cause the preset shooting point A5 to coincide with the imaging point A1.

Generally, one image is designated as a reference image during the process of image registration, and another image is an image to be registered. The purpose of registration is to enable coordinates of all points on the image to be registered to be consistent with coordinates of the points on the reference image.

In step 705, first coordinates of the treatment couch are acquired, and the first coordinates are coordinates of the treatment couch when the preset shooting point coincides with the imaging point of the IGS.

When the preset shooting point A5 coincides with the imaging point A1, the host computer 02 may acquire the first coordinates of the treatment couch 03 at this point. The first coordinates may include a first dimensional coordinate X1 extending in a width direction of the treatment couch 03, a second dimensional coordinate Y1 extending in a length direction of the treatment couch 03, and a third dimensional coordinate Z1 extending in a height direction of the treatment couch 03. That is, the first coordinates may be expressed as (X1, Y1, Z1).

In step 706, a first relative position between the imaging point and an equipment isocenter is acquired.

Since the positions of the imaging point A1 and the equipment isocenter A2 remain constant in the radiotherapy system and both the imaging point A1 and the equipment isocenter A2 are located in the coordinate system where the treatment couch 03 is located (the coordinate system may also be called as the equipment coordinate system), the host computer 02 may acquire the position coordinates of the imaging point A1 and the equipment isocenter A2 directly and may calculate a first relative position between the imaging point A1 and the equipment isocenter A2 according to the acquired position coordinates of the imaging point A1 and the equipment isocenter A2.

The first relative position may include a first distance Xiso between the imaging point A1 and the equipment isocenter A2 in the width direction of the treatment couch 03, a second distance Yiso between the imaging point A1 and the equipment isocenter A2 in the length direction of the treatment couch 03, and a third distance Ziso between the imaging point A1 and the equipment isocenter A2 in the height direction of the treatment couch 03.

For example, the positional coordinates of the imaging point A1 acquired by the host computer 02 in the equipment coordinate system are (Xi, Yi, Zi), and the positional coordinates of the acquired equipment isocenter A2 in the equipment coordinate system are (Xc, Yc, Zc). Then, the host computer 02 may calculate and obtain the first relative position (Xiso, Yiso, Ziso) of the imaging point A1 and the isocenter point A2 of the device, which satisfies: Xiso=Xi−Xc, Yiso=Yi−Yc, Ziso=Zi−Zc.

For example, the first relative position (Xiso, Yiso, Ziso) may also be acquired in a manner of mechanical design or film measuring, and the manner of acquiring the first relative position is not limited in the embodiment 2 of the present disclosure.

In step 707, a second relative position between the imaging point and the gamma angle rotation axis central point is acquired.

In the embodiment 2 of the present disclosure, the gamma angle rotation axis central point A4 may be a gamma angle rotation axis central point of the gamma angle rotation axis L of the gamma angle adjustment device 031. The second relative position may also include a first length Ix between the imaging point A1 and the gamma angle rotation axis central point A4 in a width direction of the treatment couch 03, a second length Iy between the imaging point A1 and the gamma angle rotation axis central point A4 in a length direction of the treatment couch 03 and a third length Iz between the imaging point A1 and the gamma angle rotation axis central point A4 in a height direction of the treatment couch 03. That is, the second relative position may be expressed as (Ix, Ty, Iz).

In the embodiment 2 of the present disclosure, when the treatment couch 03 is in an initial position (also called the treatment couch 03 is at zero point), that is, coordinates of the treatment couch 03 is (0, 0, 0), an initial relative position of the imaging point A1 and the gamma angle rotation axis central point A4 in a YOZ plane may be firstly acquired by the IGS system 01, and a difference value between the initial relative position and the acquired first coordinates of the treatment couch 03 is then determined as the second relative position.

The initial relative position may include a first initial relative distance X0 between the imaging point A1 and the gamma angle rotation axis central point A4 in the width direction of the treatment couch 03, a second initial relative distance Y0 between the imaging point A1 and the gamma angle rotation axis central point A4 in the length direction of the treatment couch 03, and a third initial relative distance Z0 between the imaging point A1 and the gamma angle rotation axis central point A4 in the height direction of the treatment couch 03. That is, the initial relative position may be expressed as (X0, Y0, Z0). The initial relative position (X0, Y0, Z0) may be, for example, (−0.55, 138.79, −1.98). The first coordinates may include a first dimensional coordinate X1 extending in a width direction of the treatment couch 03, a second dimensional coordinate Y1 extending in a length direction of the treatment couch 03, and a third dimensional coordinate Z1 extending in a height direction of the treatment couch 03. That is, the first coordinates may be expressed as (X1, Y1, Z1). Accordingly, the second relative position (Ix, Ty, Iz) of the imaging point A1 and the gamma angle rotation axis central point A4 determined by the host computer 02 may meet: Ix=X0−X1, Iy=Y0−Y1, Iz=Z0−Z1.

In step 708, a third relative position between the target point of the affected part and the gamma angle rotation axis central point at the gamma angle for treatment is acquired.

In the embodiment 2 of the present disclosure, the host computer 02 may determine the position of the target point A3 of the affected part according to the treatment plan firstly.

For example, before the radiotherapy, the host computer 02 may acquire the CT reconstructed images at different gamma angles for treatment. According to the CT reconstructed images, the therapist may formulate a treatment plan for the patient, which includes the position of the target point A3, and input the treatment plan to the host computer 02, so that the host computer 02 may acquire the position of the target point A3 from the treatment plan. For example, the host computer 02 may obtain the CT-DRR films at the gamma angles of 70°, 90° or 110° for treatment. Secondly, since the position of the gamma angle rotation axis central point A4 is fixed, the host computer 02 may directly obtain the position of the gamma angle rotation axis central point A4. Since the target point A3 and the gamma angle rotation axis central point A4 are located in different coordinate systems, the host computer 02 may convert the position of the acquired target point A3 and the position of the gamma angle rotation axis central point A4 into a same coordinate system to calculate the third relative position between the target point A3 and the gamma angle rotation axis central point A4.

Figure 17:
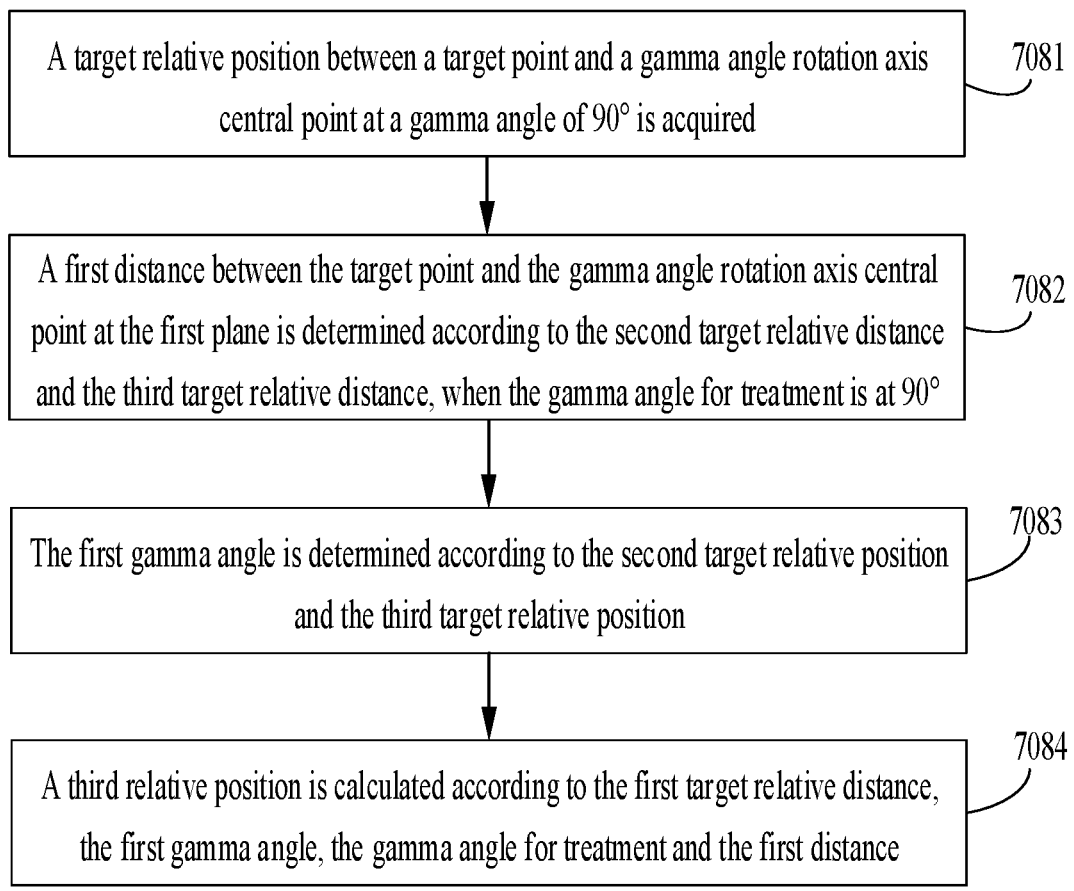
FIG. 17 is a flowchart of a method for determining a third relative position according to the embodiment 2 of the present disclosure.

FIG. 17 is a flowchart of a method for determining a third relative position according to the embodiment 2 of the present disclosure. The method can be applied to the host computer 02 as shown in FIG. 1. As shown in FIG. 17, the method may include the following steps.

In step 7081, a target relative position between a target point and a gamma angle rotation axis central point at a gamma angle of 90° is acquired.

In the embodiment 2 of the present disclosure, the target relative position may include a first target relative distance Tx90 between the target point A3 and the gamma angle rotation axis central point A4 in a width direction of the treatment couch 03, a second target relative distance Ty90 between the target point A3 and the gamma angle rotation axis central point A4 in a length direction of the treatment couch 03, and a third target relative distance Tz90 between the target point A3 and the gamma angle rotation axis central point A4 in a height direction of the treatment couch 03. That is, the initial relative position may be expressed as (Tx90, Ty90, Tz90).

For example, the embodiment 2 of the present disclosure provides a method for acquiring a target relative position between the target point A3 and the gamma angle rotation axis central point A4 when a gamma angle γ for treatment is of 90°. The method includes the following steps.

In step S1, when a gamma angle γ for treatment is of 90°, a fourth relative position between an imaging point and a gamma angle rotation axis central point.

The embodiment 2 of the present disclosure provides a method for acquiring a target relative position between a target point and a gamma angle rotation axis central point when a gamma angle for treatment is of 90°. The method includes the following steps.

In step S10, a second distance between the imaging point and the gamma angle rotation axis central point in a first plane at the gamma angle for treatment is calculated according to a second length and a third length.

The first plane may be a plane where a third axis Z extending in a length direction of the treatment couch and a second axis Y extending in a height direction of treatment couch are located, that is, the YOZ plane as shown in FIG. 1.

Figure 18:
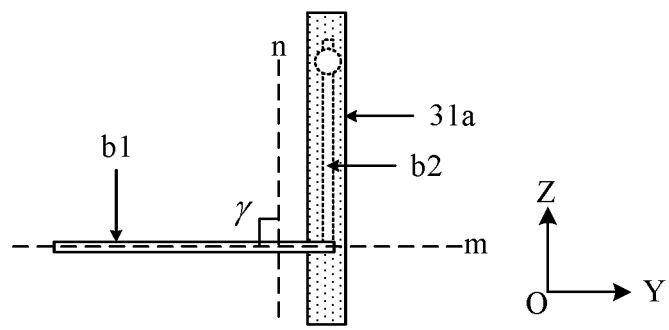
FIG. 18 is a side view of a gamma angle adjustment device according to the embodiment 2 of the present disclosure.
Figure 19:
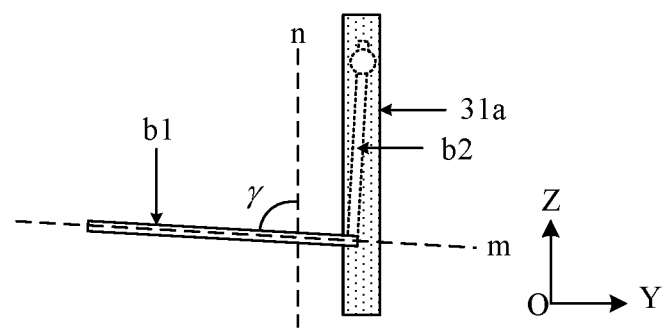
FIG. 19 is another side view of the gamma angle adjustment device according to the embodiment 2 of the present disclosure.

FIGS. 18 and 19 are a side view of a gamma angle adjustment device 031 according to the embodiment 2 of the present disclosure. In combination of FIG. 18 and FIG. 19, it can be seen that the support frame 31b may include a support panel b1 for supporting the affected part of the patient (such as, the head), and two connection rods b2 which are arranged oppositely. One end of each connection rod b2 is fixedly connected to the support panel b1, and the other end is rotatably connected to the fix frame 31a. Comparing FIG. 8 with FIG. 9, it may be seen that the connection rods b2 may drive the support panel b1 to rotate in the vertical plane (namely, the YOZ plane), thereby adjusting the gamma angle γ.

According to the aforesaid analysis, the gamma angle adjustment device 031 may only rotate in the first plane YOZ. That is, during the process of adjusting the gamma angle, the position of the target point A3 only changes in the first plane YOZ, and the coordinates of the target point A3 on the first axis X do not change. Thus, after calculating and obtaining the second relative position (Ix, Iy, Iz), the host computer 02 may firstly calculate the second distance $LI_{YOZ}$ between the imaging point A1 and the gamma angle rotation axis central point A4 in the YOZ plane at the gamma angle for treatment according to the second length Iy and the third length Iz. The second distance $LI_{YOZ}$ may satisfy: $LI_{yoz}=\sqrt{(Iy)^2+(Iz)^2}$.

In step S11, a second gamma angle is determined according to the second length and the third length.

In the embodiment 2 of the present disclosure, a second gamma angle γ2 determined by the host computer 02 according to the second length Iy and the third length Iz may meet γ2=arctan(Iz/Iy), that is, the second gamma angle γ2 may be arctangent value of a ratio of the third length Iz to the second length Iy.

In step S12, a fourth relative position is calculated according to a first length, the second gamma angle, the gamma angle for treatment and the second distance.

In the embodiment 2 of the present disclosure, the fourth relative position may include, when the gamma angle γ for treatment is of 90°, a first position Ix90 between the imaging point A1 and the gamma angle rotation axis central point A4 in the width direction of the treatment couch 03, a second position Iy90 between the imaging point A1 and the gamma angle rotation axis central point A4 in the length direction of the treatment couch 03, and a third position Iz90 between the imaging point A1 and the gamma angle rotation axis central point A4 in the height direction of the treatment couch 03. That is, the fourth relative position may be expressed as (Ix90, Iy90, Iz90). Correspondingly, the fourth relative position (Ix90, Iy90, Iz90) calculated and obtained by the host computer 02 according to the acquired gamma angle γ for treatment, the first length Ix, the second distance $LI_{YOZ}$ and the second gamma angle γ2 may satisfy:

Ix90=Ix      Formula (1);

Iy90=$LI_{yoz}$×cos(γ2+90°−γ)      Formula (2);

Iz90=$LI_{yoz}$×sin(γ2+90°−γ)      Formula (3).

With reference to the formula (1), since the position of the target point A3 only changes in the first plane YOZ during the process of adjusting the gamma angle γ, the coordinates of the target point A3 on the first axis X will not change. That is, there is no necessity to consider the relative distance between the target point A3 and the imaging point A1 on the first axis X. Thus, the first length Ix may be directly determined as the first position Ix90.

With reference to the formula (2), it may be seen that the product of the second distance $LI_{YOZ}$ and the cosine value of the second angle α2 may be determined as the second position Iy90. The second angle α2 herein may be an angle obtained by adding the second gamma angle γ2 to 90°, and then subtracting the gamma angle γ for treatment. That is, the first angle α may satisfy: α2=γ2+90°−γ.

With reference to the formula (3), it may be seen that the product of the second distance $LI_{YOZ}$ and the sine value of the second angle α2 may be determined as the third position Iz90.

In step S2, a fifth relative position between the target point and the imaging point is acquired when the gamma angle for treatment is of 90°.

In the embodiment 2 of the present disclosure, the target point A3 acquired by the host computer 02 is located in the image coordinate system, and the imaging point A1 is located in the equipment coordinate system. Thus, for the convenience of calculation, the IGS system 01 may firstly convert positional coordinates of the acquired target point A3 into the equipment coordinate system, so that the target point A3 and the imaging point A1 are located in the same coordinate system. With reference to FIG. 1, the equipment coordinate system may be a 3D coordinate system consisting of a first axis X extending in a width direction of the treatment couch 03, a second axis Y extending in a length direction of the treatment couch 03, and a third axis Z extending in a height direction of the treatment couch 03.

Correspondingly, the fifth relative position may include a distance TIx between the target point A3 and the imaging point A1 in the width direction of the treatment couch 03, a distance TIy between the target point A3 and the imaging point A1 in the length direction of the treatment couch 03, and a relative distance TIz between the target point A3 and the imaging point A1 in the height direction of the treatment couch 03. That is, the fifth relative position between the target point A3 and the imaging point A1 may be expressed as (TIx, TIy, TIz).

For example, it is assumed that, after the host computer 02 converts the position of the acquired target point A3 into the equipment coordinate system, the coordinates of the target point A3 are (Xb, Yb, Zb), and the coordinates of the acquired imaging point A1 in the equipment coordinate system are (Xi, Yi, Zi). Then, the determined fifth relative position (TIx, TIy, TIz) between the target point A3 and the imaging point A1 may satisfy: TIx=Xb−Xi, TIy=Yb−Yi, TIz=Zb−Zi.

In step S3, a sum of the fourth relative position and the fifth relative position is determined as the target relative distance.

In the embodiment 2 of the present disclosure, a first target relative distance Tx90 of the target relative distance, which is calculated and obtained by the host computer 02 according to the fourth relative position and the fifth relative position, may be Tx90=Ix90+Tix. A second target relative distance Ty90 may be Ty90=Iy90+TIy and a third target relative distance Tz90 may be Tz90=Iz90+TIz.

In step 7082, a first distance between the target point and the gamma angle rotation axis central point at the first plane is determined according to the second target relative distance and the third target relative distance, when the gamma angle for treatment is at 90°.

During the process of adjusting the gamma angle, since the position of the target point A3 may only rotate in the first plane YOZ and the coordinates of the target point A3 on the first axis X do not change, after calculating and obtaining the target relative position (Tx90, Ty90, Tz90), the host computer 02 may firstly calculate the first target distance $LT_{yoz}$ between the target point A3 and the gamma angle rotation axis central point A4 in the first plane YOZ according to the second target relative distance Ty90 and the third target relative distance Tz90. The first target distance $LT_{yoz}$ may satisfy: $LT_{YOZ}=\sqrt{(Ty90)^2+(Tz90)^2}$.

In step 7083, the first gamma angle is determined according to the second target relative position and the third target relative position.

The first gamma angle γ1 determined by the host computer 02 according to the second target relative distance Ty90 and the third target relative distance Tz90 may satisfy γ1=arctan(Tz90/Ty90). That is, the γ1 may be arctangent value of a ratio of the third target relative distance Tz90 and the second target relative distance Ty90.

In step 7084, a third relative position is calculated according to the first target relative distance, the first gamma angle, the gamma angle for treatment and the first distance.

In the embodiment 2 of the present disclosure, the third relative position may include, at the gamma angle γ for treatment, a first relative distance Tx between the target point A3 and the gamma angle rotation axis central point A4 in the width direction of the treatment couch 03, a second relative distance Ty between the target point A3 and the gamma angle rotation axis central point A4 in the length direction of the treatment couch 03, and a third relative distance Tz between the target point A3 and the gamma angle rotation axis central point A4 in the height direction of the treatment couch 03. The third relative position may be expressed as: (Tx, Ty, Tz). Correspondingly, the third relative position (Tx, Ty, Tz) calculated and obtained by the host computer 02 according to the acquired the first distance $LT_{yoz}$, the first gamma angle γ1, the gamma angle γ for treatment and the first target relative distance Tx90, and the third relative position (Tx, Ty, Tz) calculated and obtained may satisfy:

$$Tx=90 \qquad \text{Formula (4)};$$

$$Ty=LT_{yoz} \times \cos(\gamma 1+90°-\gamma) \qquad \text{Formula (5); and}$$

$$Tz=LT_{yoz} \times \sin(\gamma l+90°-\gamma) \qquad \text{Formula (6)}.$$

With reference to the formula (4), since the position of the target point A3 only changes in the first plane YOZ during the process of adjusting the gamma angle γ, the coordinates of the target point A3 on the first axis X will not change. That is, there is no necessity to consider the relative distance between the target point A3 and the imaging point A1 on the first axis X. Thus, the first target relative distance Tx90 may be directly determined as the first relative distance Tx.

With reference to the formula (5), it may be seen that the product of the distance $LT_{yoz}$ and the cosine value of the first angle α1 may be determined as the second relative distance Ty. The first angle α1 herein may be an angle obtained by adding the first gamma angle γ1 to 90°, and then subtracting the gamma angle γ for treatment. That is, the first angle α1 may satisfy:

$$\alpha 1=\gamma 1+90°-\gamma$$

With reference to the formula (6), it may be seen that the product of the first distance $LT_{yoz}$ and the sine value of the first angle α1 may be determined as the third relative distance Tz.

In step 709, when the target point coincides with the equipment isocenter, the second coordinates of the treatment couch at the gamma angle for treatment are calculated according to the first coordinates, the first relative position, the second relative position and the third relative position.

In the embodiment 2 of the present disclosure, the host computer 02 may add the first coordinates to the first relative position and then subtract the third relative position, and then add the second relative position to obtain the second coordinates of the treatment couch 03 at the gamma angle γ for treatment when the target point A3 coincides with the equipment isocenter A2. The second coordinates may also include a first dimensional coordinate Xt extending in the width direction of the treatment couch 03, a second dimensional coordinate Yt extending in the length direction of the treatment couch 03, and a third dimensional coordinate Zt extending in the width direction of the treatment couch 03. That is, the second coordinates may be expressed as (Xt, Yt, Zt), and the second coordinates (Xt, Yt, Zt) may satisfy:

$$Xt=Xl+Xiso-Tx+Ix \qquad \text{Formula (7)};$$

$$Yt=Yl+Yiso-Ty+Iy \qquad \text{Formula (8); and}$$

$$Zt=Zl+Ziso-Tz+Iz \qquad \text{Formula (9)}.$$

With reference to the formula (7), it may be seen that the first dimensional coordinate Xt is obtained by adding the first dimensional coordinate X1 in the first coordinate to the first distance Xiso and then subtracting the first relative distance Tx, and then adding the first length Ix.

With reference to the formula (8), it may be seen that the second dimensional coordinate Yt is obtained by adding the second dimensional coordinate Y1 in the first coordinate to the second distance Yiso and then subtracting the second relative distance Ty, and then adding the second length Iy.

With reference to the formula (9), it may be seen that the third dimensional coordinate Zt is obtained by adding the third coordinate Z1 in the first coordinate to the third distance Ziso and then subtracting the third relative distance Tz, and then adding the third length Iz.

In step 710, the position of the treatment couch is adjusted according to the second coordinates.

In the embodiment 2 of the present disclosure, the host computer 02 may accurately adjust the position of the treatment couch 03 according to the calculated and obtained second coordinates (Xt, Yt, Zt), which improves the accuracy of the alignment between the target point A3 and the equipment isocenter A2 at the gamma angle for treatment, and improves the accuracy of the radiotherapy.

Optionally, the sequence of the steps of the positioning method provided by the embodiment 2 of the present disclosure may be appropriately adjusted, and the steps may also be added or deleted accordingly according to the situation. For example, the steps 701 to 705 may be executed after the step 708. That is, at the gamma angle for treatment, the third relative position between the target point of the affected part and the gamma angle rotation axis central point may be obtained firstly, and then the first coordinates of the treatment couch is obtained. Any method that can be easily conceived by any one skilled in the art within the technical scope disclosed in the present disclosure shall be contained within the protection scope of the present disclosure, and therefore will not be described again.

In summary, the embodiment 2 of the present disclosure provides a positioning method. According to the method, when the target point coincides with the equipment isocenter, the second coordinates of the treatment couch at the gamma angle for treatment can be calculated according to the first coordinates of the treatment couch acquired when the preset shooting point coincides with the imaging point, the first relative position between the imaging point and the equipment isocenter, and the second relative position between the imaging point and the gamma angle rotation axis central point, and the third relative position between the target point of the affected part and the gamma angle rotation axis central point at the gamma angle for treatment. Then, the position of the treatment couch can be adjusted according to the second coordinates. Therefore, after adjusting the gamma angle during the radiotherapy, the second coordinates of the treatment couch at the adjusted gamma angle when the target point coincides with the equipment isocenter can be accurately calculated and obtained, which improves the accuracy of the alignment between the target point and the equipment isocenter at different gamma angles and improves the accuracy of the radiotherapy.

Figure 20:
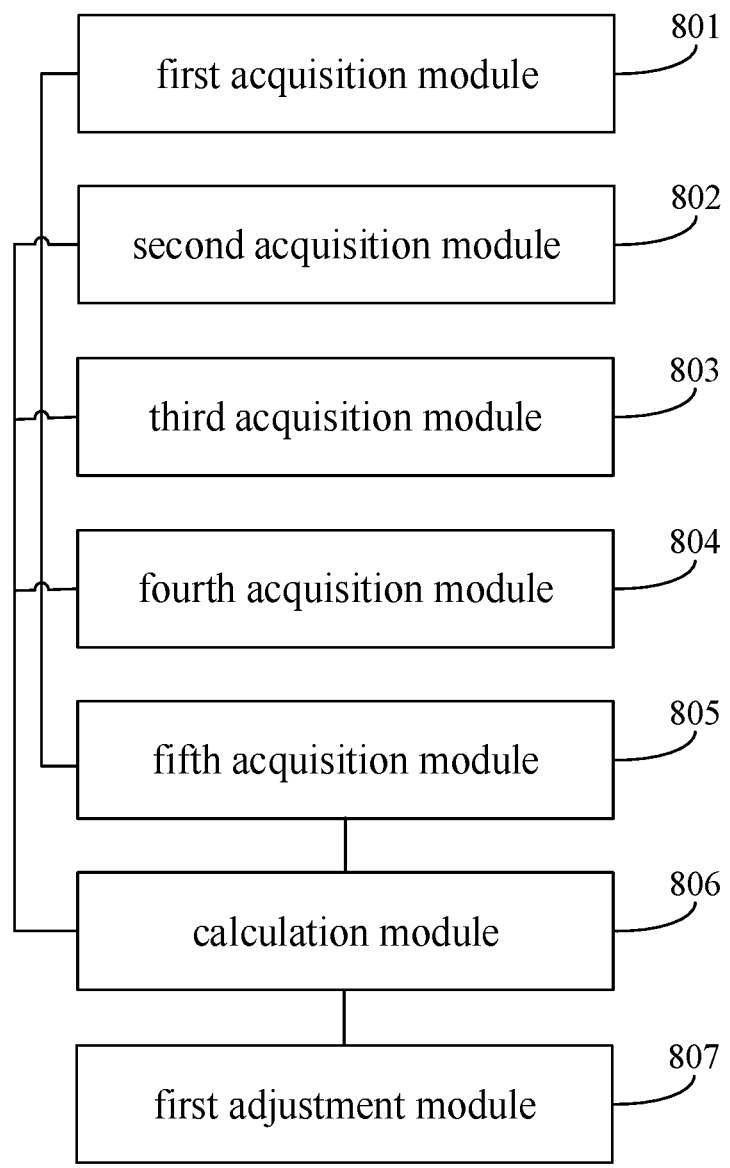
FIG. 20 is a block diagram of a positioning apparatus according to the embodiment 2 of the present disclosure.

FIG. 20 is a block diagram of a positioning apparatus according to the embodiment 2 of the present disclosure. The apparatus may be applied into the host computer 02 shown in FIG. 2. Alternatively, with reference to above description, the positioning apparatus may also be applied to the IGS system 01 or the treatment couch 03 shown in FIG. 1, which is not limited in the embodiment 2 of the present disclosure. The following embodiment 2 is illustrated by taking the positioning apparatus applied to the host computer 02 as an example. As shown in FIG. 20, the apparatus may include following modules.

A first acquisition module 801 is configured to acquire a gamma angle for treatment.

A second acquisition module 802 is configured to acquire first coordinates of a treatment couch, and the first coordinates are coordinates of the treatment couch when a preset shooting point coincides with an imaging point of an image guidance system IGS.

A third acquisition module 803 is configured to determine a first relative position between the imaging point and an equipment isocenter according to the gamma angle for treatment.

A fourth acquisition module 804 is configured to acquire a second relative position between the imaging point and a gamma angle rotation axis central point, and the gamma angle rotation axis central point is a central point of a gamma angle rotation axis of gamma angle adjustment device which is used for adjusting a gamma angle.

A fifth acquisition module 805 is configured to acquire a third relative position between the target point of the affected part and the gamma angle rotation axis central point at the gamma angle for treatment.

A calculation module 806 is configured to calculate second coordinates of the treatment couch at the gamma angle for treatment when the target point coincides with the equipment isocenter according to the first coordinates, the first relative position, the second relative position and the third relative position.

A first adjustment module 807 is configured to adjust a position of the treatment couch according to the second coordinates.

In summary, the embodiment 2 of the present disclosure provides a positioning apparatus. In the apparatus, the calculation module can calculate the second coordinates of the treatment couch at the gamma angle for treatment when the target point coincides with the equipment isocenter according to the first coordinates of the treatment couch acquired by the second acquisition module when the preset shooting point coincides with the imaging point, the first relative position between the imaging point and an equipment isocenter acquired by the third acquisition module, the second relative position between the imaging point and a gamma angle rotation axis central point acquired by the fourth acquisition module, and the third relative position between the target point of the affected part and the gamma angle rotation axis central point at the gamma angle for treatment acquired by the fifth acquisition module. Then, the first adjustment module can adjust the position of the treatment couch according to the second coordinates. Therefore, after adjusting the gamma angle during the radiotherapy, the second coordinates of the treatment couch at the adjusted gamma angle when the target point coincides with the equipment isocenter can be accurately calculated, which improves the accuracy of the alignment between the target point and the equipment isocenter at different gamma angles and improves the accuracy of the radiotherapy.

Figure 21:
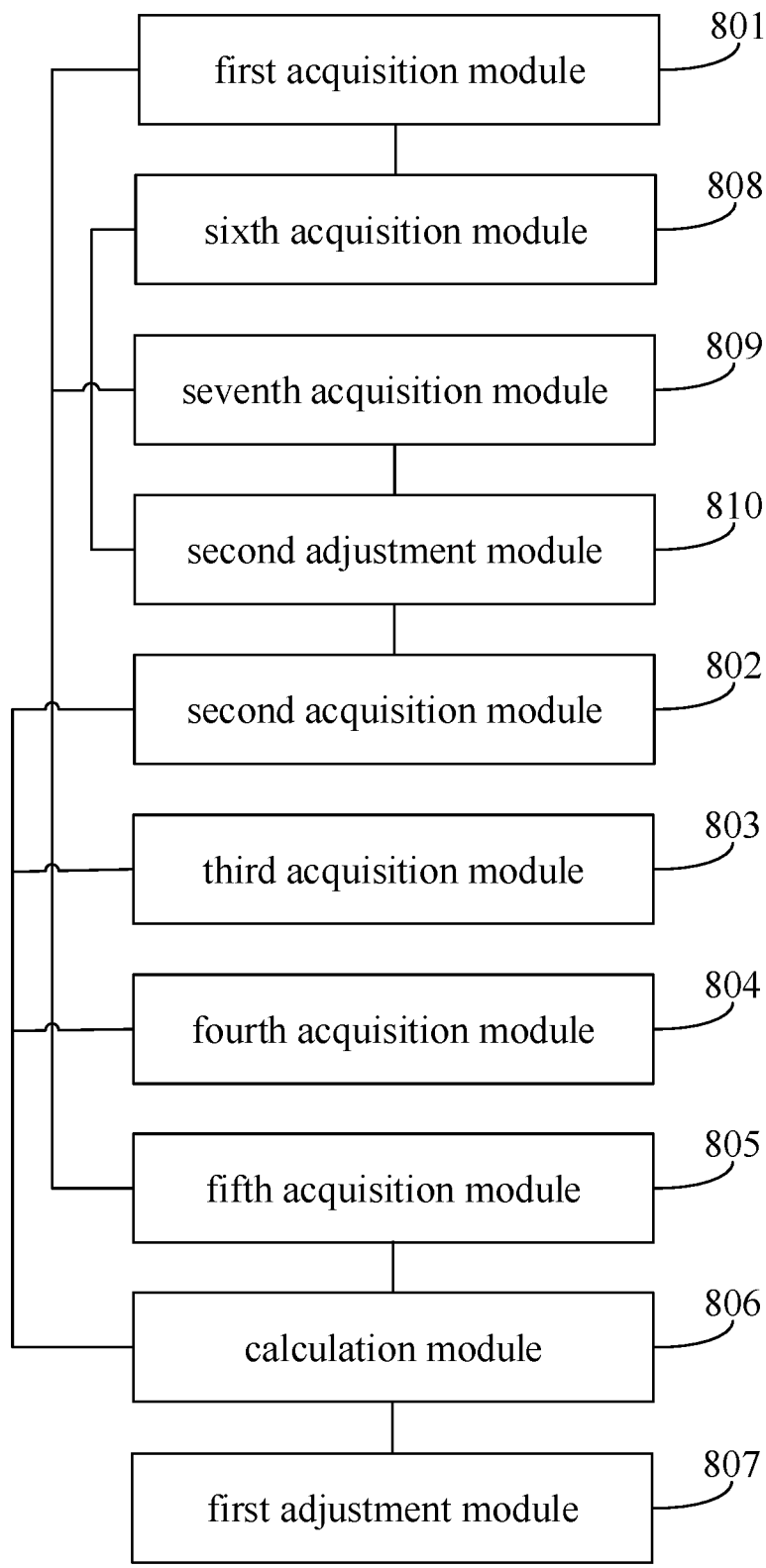
FIG. 21 is a block diagram of another positioning apparatus according to the embodiment 2 of the present disclosure.

FIG. 21 is a block diagram of another positioning apparatus according to the embodiment 2 of the present disclosure. The apparatus may be applied into the host computer 02 shown in FIG. 2. Alternatively, with reference to above description, the positioning apparatus may also be applied to the IGS system 01 or the treatment couch 03 shown in FIG. 1, which is not limited in the embodiment 2 of the present disclosure. The following embodiment 2 is illustrated by taking the positioning apparatus applied to the host computer 02 as an example. As shown in FIG. 11, the apparatus may further include following modules.

A sixth acquisition module 808 is configured to acquire a reconstructed image of the gamma angle for treatment before acquiring the first coordinates of the treatment couch, and the reconstructed image is an image reconstructed from an electronic image of the affected part acquired in advance.

A seventh acquisition module 809 is configured to acquire an IGS image of the affected part at the gamma angle for treatment, and the IGS image is an image generated by the IGS.

A second adjustment module 810 is configured to perform an image registration on the reconstructed image and the IGS image by adjusting the position of the treatment couch, so that the preset shooting point coincides with the imaging point.

Optionally, the fourth acquisition module 804 may be used to acquire an initial relative position between the imaging point and the gamma angle rotation axis central point when the treatment couch is at an initial position, and to determine a difference value between the initial relative position and the first coordinates as the second relative position.

Figure 22:
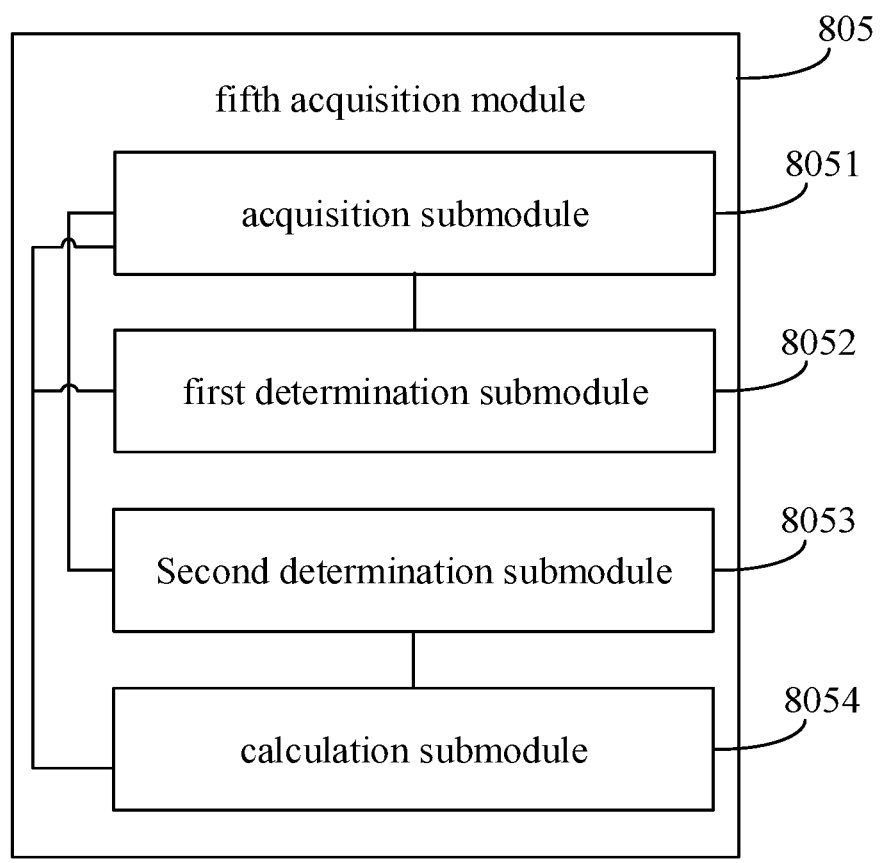
FIG. 22 is a block diagram of a fifth acquisition module according to the embodiment 2 of the present disclosure.

FIG. 22 is a block diagram of the fifth acquisition module 805 according to the embodiment 2 of the present disclosure. As shown in FIG. 22, the fifth acquisition module 805 may further include following submodules.

An acquisition submodule 8051 is configured to acquire a target relative position between the target point and the gamma angle rotation axis central point when the gamma angle for treatment is at 90°. The target relative position may include a first target relative distance between the target point and the gamma angle rotation axis central point in a width direction of the treatment couch, a second target relative distance between the target point and the gamma angle rotation axis central point in a length direction of the treatment couch, and a third target relative distance between the target point and the gamma angle rotation axis central point in a height direction of the treatment couch.

A first determination submodule 8052 is configured to determine a first distance between the target point and the gamma angle rotation axis central point in a first plane according to the second target relative distance and the third target relative distance, when the gamma angle for treatment is at 90°. The first plane is a plane where a first axis extending in the length direction of the treatment couch and a second axis extending in the height direction of the treatment couch are located.

A second determination submodule 8053 is configured to determine a first gamma angle according to the second target relative distance and the third target relative distance.

A calculation submodule 8054 is configured to calculate a third relative position according to the first target relative distance, the first gamma angle, the gamma angle for treatment and the first distance.

Optionally, the third relative position may include, at the gamma angle for treatment, a first relative distance between the target point and the gamma angle rotation axis central point in a width direction of the treatment couch, a second relative distance between the target point and the gamma angle rotation axis central point in a length direction of the treatment couch, and a third relative distance between the target point and the gamma angle rotation axis central point in a height direction of the treatment couch.

Optionally, the calculation submodule 8054 is configured to:

determine the first target relative distance as the first relative distance;

determine a product of the first distance and a cosine value of a first angle as the second relative distance, and the first angle is an angle obtained by adding the first gamma angle to 90° and then subtracting the gamma angle for treatment; and determine the product of the first distance and a sine value of the first angle as the third relative distance.

Optionally, the acquisition submodule 8051 is used to acquire a fourth relative position between the imaging point and the gamma angle rotation axis central point when the gamma angle for treatment is at 90°; and acquire a fifth relative position between the target point and the imaging point and determine a sum of the fourth relative position and the fifth relative position as the target relative position when the gamma angle for treatment is at 90°.

Optionally, the second relative position may include a first length between the imaging point and the gamma angle rotation axis central point in a width direction of the treatment couch, a second length between the imaging point and the gamma angle rotation axis central point in a length direction of the treatment couch and a third length between the imaging point and the gamma angle rotation axis central point in a height direction of the treatment couch.

Accordingly, that the acquisition submodule 8051 acquires the fourth relative position between the imaging point and the gamma angle rotation axis central point may include:

at the gamma angle for treatment, a second distance between the imaging point and the gamma angle rotation axis central point in the first plane is calculated according to the second length and the third length;

a second gamma angle is determined according to the second length and the third length; and the fourth relative position is calculated according to the first length, the second gamma angle, the gamma angle for treatment and the second distance.

Optionally, the fourth relative position may include, when the gamma angle for treatment is at 90°, a first position between the imaging point and the gamma angle rotation axis central point in a width direction of the treatment couch, a second position between the imaging point and the gamma angle rotation axis central point in a length direction of the treatment couch, and a third position between the imaging point and the gamma angle rotation axis central point in a height direction of the treatment couch.

Accordingly, that the acquisition submodule 8051 calculates the fourth relative position according to the first length, the second gamma angle, the gamma angle for treatment and the second distance may include:

the first distance is determined as the first position;

a product of the second distance and a cosine value of a second angle is determined as the second position, and the second angle is an angle obtained by adding the second gamma angle to 90° and then subtracting the gamma angle for treatment; and the product of the second distance and a sine value of the second angle is determined as the third position.

Optionally, the calculation module 806 is configured to obtain the second coordinates of the treatment couch by adding the first coordinates to the first relative position and then subtracting the third relative position, and then adding the second relative position.

In summary, the embodiment 2 of the present disclosure provides a positioning apparatus. In the apparatus, the calculation module can calculate the second coordinates of the treatment couch at the gamma angle for treatment when the target point coincides with the equipment isocenter according to the first coordinates of the treatment couch acquired by the second acquisition module when the preset shooting point coincides with the imaging point, the first relative position between the imaging point and an equipment isocenter acquired by the third acquisition module, the second relative position between the imaging point and a gamma angle rotation axis central point acquired by the fourth acquisition module, and the third relative position between the target point of the affected part and the gamma angle rotation axis central point at the gamma angle for treatment acquired by the fifth acquisition module. Then, the first adjustment module can adjust the position of the treatment couch according to the second coordinates. Therefore, after adjusting the gamma angle during the radiotherapy, the second coordinates of the treatment couch at the adjusted gamma angle when the target point coincides with the equipment isocenter can be accurately calculated, which improves the accuracy of the alignment between the target point and the equipment isocenter at different gamma angles and improves the accuracy of the radiotherapy.

With regard to the positioning apparatus in the forgoing described embodiments, the specific manner in which the respective modules perform the operations has been described in detail in the embodiments of the method, and will not be explained in detail herein.

The embodiment 2 of the present disclosure provides a positioning apparatus. The positioning apparatus may include a processor and a memory in which instructions are stored, and the instructions may be loaded and executed by the processor to implement the positioning method shown in any one of FIGS. 14, 15, and 17.

Furthermore, the embodiment 2 of the present disclosure provides a storage medium in which instructions are stored. When the storage medium runs at a processing component, the processing component is actuated to execute the positioning method shown in any one of FIGS. 14, 15, and 17.

The embodiment 2 of the present disclosure may further provide a radiotherapy system, which includes a positioning apparatus shown in any one of FIG. 20 and FIG. 21.

A person skilled in the art may clearly understand that the specific working process of the apparatus and modules described above may refer to the corresponding process in the aforesaid method embodiment, and details will not be described herein again for the convenience and brevity of the description.

The above are just the preferred embodiments of the present disclosure, which will not limit the present disclosure. Any modifications, equivalent replacements and improvements made within the spirits and principles of the present disclosure shall all fall in the protection scope of the present disclosure.

What is claimed is:

1. A positioning method realized by a computer, comprising:

acquiring a gamma angle for treatment;

acquiring first coordinates of a treatment couch, wherein the first coordinates are coordinates of the treatment couch when a preset shooting point coincides with an imaging point of an image guidance system (IGS);

acquiring a first relative position between the imaging point and an equipment isocenter;

acquiring a second relative position between the imaging point and a gamma angle rotation axis central point, wherein the gamma angle rotation axis central point is a central point of a gamma angle rotation axis of a gamma angle adjustment device which is used for adjusting a gamma angle;

acquiring a third relative position between a target point of an affected part and the gamma angle rotation axis central point at the gamma angle for treatment;

calculating second coordinates of the treatment couch at the gamma angle for treatment according to the first coordinates, the first relative position, the second relative position, and the third relative position, when the target point coincides with the equipment isocenter; and adjusting the position of the treatment couch according to the second coordinates.

2. The method according to claim 1, wherein before acquiring the first coordinates of the treatment couch the method further comprises:

acquiring a reconstructed image of the gamma angle for treatment, wherein the reconstructed image is an image reconstructed from an electronic image of the affected part acquired in advance;

acquiring an IGS image of the affected part at the gamma angle for treatment, wherein the IGS image is an image generated by the IGS; and performing an image registration on the reconstructed image and the IGS image by adjusting the position of the treatment couch, such that the preset shooting point coincides with an imaging point.

3. The method according to claim 1, wherein the acquiring the second relative position between the imaging point and the gamma angle rotation axis central point comprises:

acquiring an initial relative position between the imaging point and the gamma angle rotation axis central point when the treatment couch is at an initial position; and determining a difference value between the initial relative position and the first coordinates as the second relative position.

4. The method according to claim 1, wherein the acquiring the third relative position between the target point of the affected part and the gamma angle rotation axis central point at the gamma angle for treatment comprises:

acquiring a target relative position between the target point and the gamma angle rotation axis central point when the gamma angle for treatment is at 90°, wherein the target relative position comprises a first target relative distance between the target point and the gamma angle rotation axis central point in a width direction of the treatment couch, a second target relative distance between the target point and the gamma angle rotation axis central point in a length direction of the treatment couch, and a third target relative distance between the target point and the gamma angle rotation axis central point in a height direction of the treatment couch;

determining a first distance between the target point and the gamma angle rotation axis central point in a first plane according to the second target relative distance and the third target relative distance, when the gamma angle for treatment is at 90°, wherein the first plane is a plane where a first axis extending in the length direction of the treatment couch and a second axis extending in the height direction of the treatment couch are located;

determining a first gamma angle according to the second target relative distance and the third target relative distance; and calculating a third relative position according to the first target relative distance, the first gamma angle, the gamma angle for treatment and the first distance.

5. The method according to claim 4, wherein the third relative position comprises, at the gamma angle for treatment, a first relative distance between the target point and the gamma angle rotation axis central point in a width direction of the treatment couch, a second relative distance between the target point and the gamma angle rotation axis central point in a length direction of the treatment couch, and a third relative distance between the target point and the gamma angle rotation axis central point in a height direction of the treatment couch; and wherein the calculating the third relative position according to the first target relative distance, the first gamma angle, the gamma angle for treatment and the first distance comprises:

determining the first target relative distance as the first relative distance;

determining a product of the first distance and a cosine value of a first angle as the second relative distance, wherein the first angle is an angle obtained by adding the first gamma angle to 90° and then subtracting the gamma angle for treatment; and determining the product of the first distance and a sine value of the first angle as the third relative distance.

6. The method according to claim 4, wherein the acquiring a target relative position between the target point and the gamma angle rotation axis central point when the gamma angle for treatment is at 90° comprises:

acquiring a fourth relative position between the imaging point and the gamma angle rotation axis central point when the gamma angle for treatment is at 90°;

acquire a fifth relative position between the target point and the imaging point when the gamma angle for treatment is at 90°; and determining a sum of the fourth relative position and the fifth relative position as the target relative position.

7. The method according to claim 6, wherein the second relative position comprises a first length between the imaging point and the gamma angle rotation axis central point in the width direction of the treatment couch, a second length between the imaging point and the gamma angle rotation axis central point in the length direction of the treatment couch and a third length between the imaging point and the gamma angle rotation axis central point in the height direction of the treatment couch; and wherein the acquiring the fourth relative position between the imaging point and the gamma angle rotation axis central point when the gamma angle for treatment is at 90° comprises:

calculating, at the gamma angle for treatment, a second distance between the imaging point and the gamma angle rotation axis central point in the first plane according to the second length and the third length;

determining a second gamma angle according to the second length and the third length; and calculating the fourth relative position according to the first length, the second gamma angle, the gamma angle for treatment and the second distance.

8. The method according to claim 7, wherein the fourth relative position may include, when the gamma angle for treatment is at 90°, a first position between the imaging point and the gamma angle rotation axis central point in a width direction of the treatment couch, a second position between the imaging point and the gamma angle rotation axis central point in a length direction of the treatment couch, and a third position between the imaging point and the gamma angle rotation axis central point in a height direction of the treatment couch; and wherein the calculating the fourth relative position according to the first length, the second gamma angle, the gamma angle for treatment and the second distance comprises:

determining the first distance as the first position;

determining a product of the second distance and a cosine value of a second angle as the second position, wherein the second angle is an angle obtained by adding the second gamma angle to 90° and then subtracting the gamma angle for treatment; and determining the product of the second distance and a sine value of the second angle as the third position.

9. The method according to claim 1, wherein the calculating second coordinates of the treatment couch at the gamma angle for treatment according to the first coordinates, the first relative position, the second relative position, and the third relative position, when the target point coincides with the equipment isocenter comprises:

obtaining the second coordinates of the treatment couch by adding the first coordinates to the first relative position and then subtracting the third relative position, and then adding the second relative position.

10. A radiotherapy system, comprising:

a treatment gantry, configured to carry a ray source to emit rays;

an image guidance system (IGS), comprising at least one group of a detector and a tube that are disposed opposite to each other;

a treatment couch, configured to carry and move a patient; and a control equipment, configured to control the IGS to obtain an IGS image at a current gamma angle, perform an image registration on the IGS image and an electronic image and adjust a position of the treatment couch based on an image registration result, after the treatment couch is moved to a first coordinates; and wherein the control equipment is further configured to:

acquire a gamma angle for treatment;

acquire first coordinates of a treatment couch, wherein the first coordinates are coordinates of the treatment couch when a preset shooting point coincides with an imaging point of the IGS;

acquire a first relative position between the imaging point and an equipment isocenter;

acquire a second relative position between the imaging point and a gamma angle rotation axis central point, wherein the gamma angle rotation axis central point is a central point of a gamma angle rotation axis of a gamma angle adjustment device which is used for adjusting a gamma angle;

acquire a third relative position between a target point of an affected part and the gamma angle rotation axis central point at the gamma angle for treatment;

calculate second coordinates of the treatment couch at the gamma angle for treatment according to the first coordinates, the first relative position, the second relative position, and the third relative position, when the target point coincides with the equipment isocenter; and adjust the position of the treatment couch according to the second coordinates.

11. The radiotherapy system according to claim 10, wherein the control equipment is further configured to:

acquire a gamma angle for treatment;

acquire first coordinates of a treatment couch, wherein the first coordinates are coordinates of the treatment couch when a preset shooting point coincides with an imaging point of the IGS;

acquire an IGS image at a current gamma angle for treatment of the treatment couch, based on the first coordinates of the treatment couch;

acquire an electronic image at the current gamma angle for treatment; and perform an image registration on the IGS image at the current gamma angle for treatment and the electronic image at the current gamma angle for treatment and adjust the position of the treatment couch based on an image registration result.

12. A positioning method realized by a computer, comprising:

acquiring a gamma angle for treatment;

acquiring first coordinates of a treatment couch, wherein the first coordinates are coordinates of the treatment couch when a preset shooting point coincides with an imaging point of an image guidance system (IGS);

acquiring an IGS image at a current gamma angle for treatment of the treatment couch, based on the first coordinates of the treatment couch;

acquiring an electronic image at the current gamma angle for treatment;

performing an image registration on the IGS image at the current gamma angle for treatment and the electronic image at the current gamma angle for treatment and adjusting the position of the treatment couch based on an image registration result;

acquiring a first relative position between the imaging point and an equipment isocenter;

adjusting the position of the treatment couch according to the first relative position and the first coordinates;

acquiring a second relative position between the imaging point and a gamma angle rotation axis central point, wherein the gamma angle rotation axis central point is a central point of a gamma angle rotation axis of a gamma angle adjustment device which is used for adjusting a gamma angle;

acquiring a third relative position between a target point of an affected part and the gamma angle rotation axis central point at the gamma angle for treatment; and adjusting the position of the treatment couch according to the first coordinates, the first relative position, the second relative position and the third relative position.

13. The method according to claim 12, comprising:

reconstructing an image according to an electronic image of the affected part acquired in advance; and performing an image registration on a reconstructed image and the IGS image.

* * * * *